United States Patent
Tam et al.

(10) Patent No.: US 9,308,222 B2
(45) Date of Patent: Apr. 12, 2016

(54) FORMULAS COMPRISING HIGHLY SOLUBLE ELEMENTS AND VITAMINS FOR THE PREVENTION AND AMELIORATION OF OSTEOPOROSIS

(76) Inventors: Yun Kau Tam, Hong Kong (CN); Ge Lin, Hong Kong (CN)

( * ) Notice: Subject to any disclaimer, the term of this patent is extended or adjusted under 35 U.S.C. 154(b) by 592 days.

(21) Appl. No.: 12/845,301

(22) Filed: Jul. 28, 2010

(65) Prior Publication Data

US 2010/0292194 A1    Nov. 18, 2010

Related U.S. Application Data

(63) Continuation-in-part of application No. PCT/IB2009/005042, filed on Jan. 28, 2009.

(60) Provisional application No. 61/023,997, filed on Jan. 28, 2008.

(51) Int. Cl.

| A61K 33/06 | (2006.01) |
|---|---|
| A23L 1/303 | (2006.01) |
| A23L 1/304 | (2006.01) |
| A61K 31/593 | (2006.01) |
| A61K 33/30 | (2006.01) |
| A61K 35/02 | (2015.01) |
| A61K 45/06 | (2006.01) |
| A23L 1/302 | (2006.01) |
| A23L 1/29 | (2006.01) |
| A61K 31/19 | (2006.01) |
| A61K 35/60 | (2006.01) |
| A23L 2/02 | (2006.01) |
| A61K 9/20 | (2006.01) |

(52) U.S. Cl.
CPC ............... *A61K 33/06* (2013.01); *A23L 1/296* (2013.01); *A23L 1/302* (2013.01); *A23L 1/303* (2013.01); *A23L 1/304* (2013.01); *A23L 1/3045* (2013.01); *A23L 2/02* (2013.01); *A61K 9/20* (2013.01); *A61K 9/2095* (2013.01); *A61K 31/19* (2013.01); *A61K 31/593* (2013.01); *A61K 33/30* (2013.01); *A61K 35/02* (2013.01); *A61K 35/60* (2013.01); *A61K 45/06* (2013.01); *A23V 2002/00* (2013.01)

(58) Field of Classification Search
None
See application file for complete search history.

(56) References Cited

U.S. PATENT DOCUMENTS

| 5,075,499 | A | 12/1991 | Walsdorf et al. |
|---|---|---|---|
| 5,514,382 | A | 5/1996 | Sultenfuss |
| 5,654,011 | A | 8/1997 | Jackson et al. |
| 5,698,222 | A | 12/1997 | Mazer et al. |
| 5,879,698 | A | 3/1999 | Ellenbogen et al. |
| 6,716,454 | B2 | 4/2004 | Meignant et al. |
| 6,790,462 | B2 | 9/2004 | Hendricks |
| 7,029,703 | B2 | 4/2006 | Krumhar et al. |
| 2003/0190369 | A1 | 10/2003 | Lovett |
| 2005/0053673 | A1 | 3/2005 | Netke et al. |
| 2005/0181069 | A1* | 8/2005 | McCleary ............... 424/686 |
| 2006/0003981 | A1* | 1/2006 | Fine et al. ............... 514/184 |
| 2006/0188607 | A1 | 8/2006 | Schramm |
| 2007/0141170 | A1* | 6/2007 | Lang ............... 424/638 |
| 2009/0297599 | A1 | 12/2009 | Viragh et al. |
| 2011/0312923 | A1 | 12/2011 | Tam et al. |

FOREIGN PATENT DOCUMENTS

| AU | 2010212456 | 9/2010 |
|---|---|---|
| CA | 2712647 | 8/2009 |
| CN | 1027419 C | 2/1992 |
| CN | 1082836 A | 3/1994 |
| CN | 1082897 | 3/1994 |
| CN | 1242985 | 2/2000 |
| CN | 1488359 A | 4/2004 |
| CN | 101925357 A | 12/2010 |
| EP | 2257300 | 12/2010 |
| HK | 1149206 A | 9/2011 |
| IN | 1767/MUMNP/2010 | 1/2011 |
| JP | 10014535 A | 1/1998 |
| JP | 2008013469 A | 1/2008 |
| JP | 2011510922 A | 4/2011 |
| KR | 20100107468 A | 10/2010 |
| NZ | 585408 A | 5/2010 |
| SG | 162850 A | 8/2010 |
| TW | 403660 B | 9/2000 |
| TW | 200640479 A | 12/2006 |
| TW | 200711648 A | 4/2007 |
| TW | 200829246 A | 7/2008 |
| TW | I331032 | 10/2010 |
| TW | 201210629 | 3/2012 |
| WO | 2007115973 A2 | 10/2007 |

(Continued)

OTHER PUBLICATIONS

Trinidad et al. (Am J Clin Nutr 1996; 63; 574-8), see abstract and p. 577, second column, last paragraph.*

(Continued)

*Primary Examiner* — Jeffrey S Lundgren
*Assistant Examiner* — William Lee
(74) *Attorney, Agent, or Firm* — Law Offices of Albert Wai-Kit Chan, PLLC

(57) ABSTRACT

The present invention provides formulas of elemental compositions encompassing acetate salts of calcium, magnesium and zinc along with vitamin $D_3$. The acetate salts could be extracted from natural sources such as pearls, coral, and oyster or compounded using synthetic materials. The dosage and ratio of calcium to magnesium was estimated using in vitro and in vivo estimations. The dosage for promoting bone health and alleviation of osteoporosis is about a quarter to a third of the conventional dose.

8 Claims, 16 Drawing Sheets

(56) References Cited

FOREIGN PATENT DOCUMENTS

| | | |
|---|---|---|
| WO | WO 2009/095798 A2 | 8/2009 |
| WO | 2013014654 A2 | 1/2013 |

OTHER PUBLICATIONS

PCT International Search Report, Aug. 27, 2009, for International Application No. PCT/IB2009/005042, filed Jan. 28, 2009.
PCT Written Opinion of the International Searching Authority, Aug. 27, 2009, for International Application No. PCT/IB2009/005042, filed Jan. 28, 2009.
United States Office Action, Dec. 5, 2014, for U.S. Appl. No. 14/234,622, filed Jan. 23, 2014.
Abraham GE and Grewal H (1990) A total dietary program emphasizing magnesium instead of calcium. Effect on the mineral density of calcaneous bone in postmenopausal women on hormonal therapy. J Reprod Med 35:503-507.
Abrams SA and Atkinson SA (2003) Calcium, magnesium, phosphorus and vitamin D fortification of complementary foods. J Nutr 133:2994S-2999S.
Abrams SA, Griffin IJ and Herman S (2002) Using stable isotopes to assess the bioavailability of minerals in food fortification programs. Food Nutr Bull 23:158-165.
Angus RM, Pocock NA and Eisman JA (1988a) Nutritional intake of pre- and postmenopausal Australian women with special reference to calcium. Eur J Clin Nutr 42:617-625.
Angus RM, Sambrook PN, Pocock NA and Eisman JA (1988b) Dietary intake and bone mineral density. Bone Miner 4:265-277.
Bass M, Ford MA, Brown B, Mauromoustakos A and Keathley RS (2006) Variables for the prediction of femoral bone mineral status in American women. South Med J 99:115-122.
Basso Le, Ubbink JB, Delport R, Spies J and Vermaak WJ (2000) Effect of magnesium supplementation on the fractional intestinal absorption of 45CaCI2 in women with a low erythrocyte magnesium concentration. Metabolism 49:1092-1096.
Bo-Linn GW, Davis GR, Buddrus DJ, Morawski SG, Santa Ana C and Fordtran JS (1984) An evaluation of the importance of gastric acid secretion in the absorption of dietary calcium. J Clin Invest 73:640-647.
Bronner F and Pansu D (1999) Nutritional aspects of calcium absorption. J Nutr 129:9-12.
Bronner F, Slepchenko B, Wood RJ and Pansu D (2003) The role of passive transport in calcium absorption. J Nutr 133:1426; author reply 1427.
Cai J, Zhang Q, Wastney ME and Weaver CM (2004) Calcium bioavailability and kinetics of calcium ascorbate and calcium acetate in rats. Exp Biol Med (Maywood) 229:40-45.
Celotti F and Bignamini A (1999) Dietary calcium and mineral/vitamin supplementation: a controversial problem. J Int Med Res 27:1-14.
Charoenphandhu N, Tudpor K, Pulsook N and Krishnamra N (2006) Chronic metabolic acidosis stimulated transcellular and solvent drag-induced calcium transport in the duodenum of female rats. Am J Physiol Gastrointest Liver Physiol 291:G446-455.
Coudray C, Rambeau M, Feillet-Coudray C, Gueux E, Tressol JC, Mazur A and Rayssiguier Y (2005) Study of magnesium bioavailability from ten organic and inorganic Mg salts in Mg-depleted rats using a stable isotope approach. Magnes Res 18:215-223.
Hanzlik RP, Fowler SC and Fisher DH (2005) Relative bioavailability of calcium from calcium formate, calcium citrate, and calcium carbonate. J Pharmacol Exp Ther 313:1217-1222.
Heaney RP (1993a) Nutritional factors in osteoporosis. Annu Rev Nutr 13:287-316.
Heaney RP (1993b) Thinking straight about calcium. N Engl J Med 328:503-505.
Heaney RP, Dowell MS, Bierman J, Hale CA and Bendich A (2001) Absorbability and cost effectiveness in calcium supplementation. J Am Coll Nutr 20:239-246.
Hunt CD and Johnson LK (2007) Calcium requirements: new estimations for men and women by cross-sectional statistical analyses of calcium balance data from metabolic studies. Am J Clin Nutr 86:1054-1063.
Ilich JZ, Brownbill RA and Tamborini L (2003) Bone and nutrition in elderly women: protein, energy, and calcium as main determinants of bone mineral density. Eur J Clin Nutr 57:554-565.
Ilich JZ and Kerstetter JE (2000) Nutrition in bone health revisited: a story beyond calcium. J Am Coll Nutr 19:715-737.
Kanders B, Dempster DW and Lindsay R (1988) Interaction of calcium nutrition and physical activity on bone mass in young women. J Bone Miner Res 3:145-149.
Lee HH, Prasad AS, Brewer GJ and Owyang C (1989) Zinc absorption in human small intestine. Am J Physiol 256: G87-91.
Lowe NM, Lowe NM, Fraser WD and Jackson MJ (2002) Is there a potential therapeutic value of copper and zinc for osteoporosis? Proc Nutr Soc 61:181-185.
McCormick CC (2002) Passive diffusion does not play a major role in the absorption of dietary calcium in normal adults. J Nutr 132:3428-3430.
Mineo H, Amano M, Minaminida K, Chiji H, Shigematsu N, Tomita F and Hara H (2006) Two-week feeding of difructose anhydride III enhances calcium absorptive activity with epithelial cell proliferation in isolated rat cecal mucosa. Nutrition 22:312-320.
Mutlu M, Argun M, Kilic E, Saraymen R and Yazar S (2007) Magnesium, zinc and copper status in osteoporotic, osteopenic and normal post-menopausal women. J Int Med Res 35:692-695.
Record IR, Record SJ, Dreosti IE and Rohan TE (1985) Dietary zinc intake of pre-menopausal women. Hum Nutr Appl Nutr 39:363-369.
Riis B, Thomsen K and Christiansen C (1987) Does calcium supplementation prevent postmenopausal bone loss? A double-blind, controlled clinical study. N Engl J Med 316:173-177.
Saltman PD and Strause LG (1993) The role of trace minerals in osteoporosis. J Am Coll Nutr 12:384-389.
Seelig MS, Altura BM and Altura BT (2004) Benefits and risks of sex hormone replacement in postmenopausal women. J Am Coll Nutr 23:482S-496S.
Smith JC, Jr., Morris ER and Ellis R (1983) Zinc: requirements, bioavailabilities and recommended dietary allowances. Prog Clin Biol Res 129:147-169.
Tsugawa N, Okano T, Higashino R, Kimura T, Oshio Y, Teraoka Y, Igarashi C, Ezawa I and Kobayashi T (1995) Bioavailability of calcium from calcium carbonate, DL-calcium lactate, L-calcium lactate and powdered oyster shell calcium in vitamin D-deficient or -replete rats. Biol Pharm Bull 18:677-682.
Tsugawa N, Yamabe T, Takeuchi A, Kamao M, Nakagawa K, Nishijima K and Okano T (1999) Intestinal absorption of calcium from calcium ascorbate in rats. J Bone Miner Metab 17:30-36.
Wasserman RH (2004) Vitamin D and the dual processes of intestinal calcium absorption. J Nutr 134:3137-3139.
IPOS Search Report, Jul. 7, 2011, for Singapore App'l No. 201003257-1, filed Jan. 28, 2009.
IPOS Written Opinion, Jul. 7, 2011, for Singapore App'l No. 201003257-1, filed Jan. 28, 2009.
New Zealand Examiner's Report, Feb. 23, 2011, for New Zealand App'l No. 585408, filed May 7, 2010.
Extended European Search Report, Mar. 19, 2012, for European App'l No. 09706709.4, filed Aug. 14, 2010.
Chinese Office Action, Jun. 23, 2011, for Chinese App'l No. 101925357, filed Jul. 26, 2010 (w/English translation).
Chinese Office Action, Feb. 15, 2012, for Chinese App'l No. 101925357, filed Jul. 26, 2010 (w/English translation).
Braam Lajlm, Knapen MHJ, Geusens P, Brouns F, Hamulyak K, Gerichhausen MJW and Vermeer C (2003) Vitamin K1 supplementation retards bone loss in postmenopausal women between 50 and 60 years of age. Calcif Tissue Int 73: 21-26.
Christakos S, Dhawan P, Porta A, Mady LJ and Seth T (2011) Vitamin D and intestinal calcium absorption. Moll Cell Endrocrinol [Epub ahead of print].
Heaney RP, Dowell MS and Barger-Lux MJ (1999) Absorption of calcium as the carbonate and citrate salts, with some observations on method. Osteoporos Int 9:19-23.

(56) References Cited

OTHER PUBLICATIONS

IPOS Written Opinion, Jul. 12, 2012, for Singapore App'l No. 201003257-1, filed Jan. 28, 2009.
Grant et al., 2005, "Oral Vitamin D3 and Calcium for Secondary Prevention of Low-Trauma Fractures in Elderly People (Randomised Evaluation of Calcium or Vitamin D, Record): A randomised Placebo-controlled trial", Lancet, vol. 365 (9471): 1621-1628 (abstract only).
Heaney et al., 2000, "Bioavailability of the Calcium in Fortified Soy Imitation Milk, With some Observations on Method", The American Journal of Clinical Nutrition, vol. 71:1166-1169.
Pansu et al., 1993, "Nutrient Requirements and Interactions: Solubility and Intestinal Transit Time Limit Calcium Absorption in Rats", J. Nutr. vol. 123: 1396-1404.
EP Communication Art 94(3) EPC, Dec. 5, 2012, for European App'l No. 09706709.4, filed Aug. 14, 2010.
Indian Examination Report, Sep. 14, 2012, for Indian App'l No. 1767/MUMNP/2010, filed Aug. 19, 2010.
United States Office Action, Oct. 12, 2012, for U.S. Appl. No. 13/193,194, filed Jul. 28, 2011.
PCT International Search Report, Nov. 1, 2011, for PCT App'l No. WO 2013/014654, filed Jul. 27, 2012.
PCT Written Opinion, Nov. 1, 2011, for PCT App'l No. WO 2013/014654, filed Jul. 27, 2012.
United States Office Action, Feb. 19, for U.S. Appl. No. 13/193,194, filed Jul. 28, 2011.
Australian Examination Report, May 9, 2013, for Australian App'l No. 2012288401, filed Apr. 10, 2013.
European Communication Art 94(3) EPC, Apr. 16, 2013, for European App'l No. 09706709.4, filed Aug. 14, 2010.
Chinese Office Action, Jul. 25, 2013, for Chinese app'l 201210424751.7, filed Oct. 30, 2012 (with Eng translation).
Canadian Examiner's Report, Jul. 30, 2013, for Canadian App'l No. 2816207, filed May 17, 2013.
United States Office Action, Oct. 1, for U.S. Appl. No. 13/193,194, filed Jul. 28, 2011.
New Zealand Notice of Acceptance, May 17, 2012, for New Zealand App'l No. 585408, filed May 7, 2010.
Chinese Notification for the Grant of Invention Right, Aug. 28, 2012, for Chinese App'l No. 200980103115.0, filed Jul. 26, 2010.
Australian Notice of Acceptance, Jul. 22, 2013, for Australian App'l No. 2012288401, filed Apr. 10, 2013.
Indian Hearing Notice, Sep. 19, 2013, for Indian App'l No. 1767/MUMNP/2010, filed Aug. 19, 2010.
Japanese Notice of Allowance, Oct. 21, 2013, for Japanese App'l No. app'l 2010-054589, filed Jul. 26, 2010.
Indian Notice of Grant, Feb. 28, 2014, for Indian App'l No. 1767/MUMNP/2010, filed Aug. 19, 2010.
Canadian Notice of Allowance, Mar. 3, 2014, for Canadian App'l No. 2816207, filed May 17, 2013.
European Communication—Intention to Grant, Mar. 11, 2014, for European App'l No. 09706709.4, filed Aug. 14, 2010.
Chinese Office Action, Mar. 7, 2014, for Chinese app'l 201210424751.7, filed Oct. 30, 2012 (with Eng translation).
Japanese Office Action, Aug. 5, 2015, for JP Application No. 2013-237451, filed Nov. 15, 2013.

* cited by examiner

Figure 5
A.
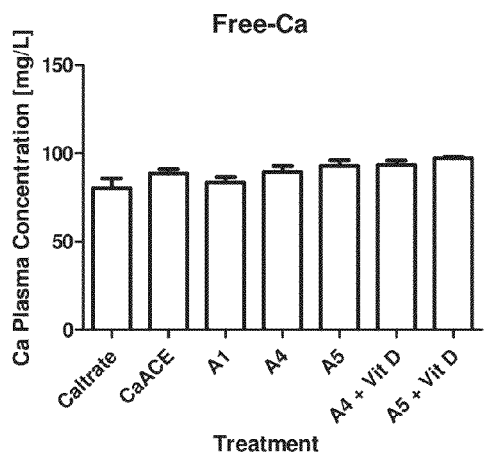
B.
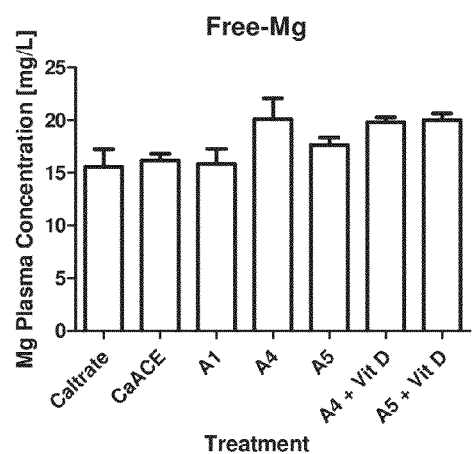
C.
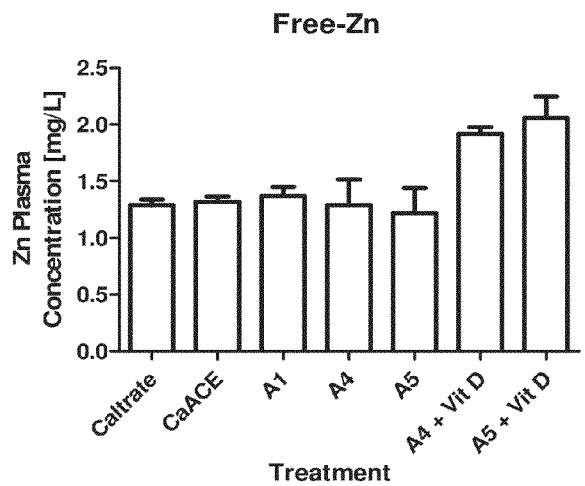

FORMULAS COMPRISING HIGHLY SOLUBLE ELEMENTS AND VITAMINS FOR THE PREVENTION AND AMELIORATION OF OSTEOPOROSIS

This application is a Continuation-in-part of International Application PCT/IB2009/005042, filed Jan. 28, 2009, which claims benefit of U.S. Provisional Application No. 61/023,997, filed Jan. 28, 2008. The entire contents and disclosures of the preceding applications are incorporated by reference into this application.

Throughout this application, various references are referred to and disclosures of these publications in their entireties are hereby incorporated by reference into this application to more fully describe the state of the art to which this invention pertains.

BACKGROUND OF THE INVENTION

Calcium is the major element in bones. Over 99% of the body's calcium resides in bones. Approximately 80-90% of bone mineral content is comprised of calcium and phosphorus. Adequate intake of calcium from diet is necessary for bone growth and maintenance. Osteoporosis is a disease caused by a significant loss of bone mass which leads to increased susceptibility to fracture. This condition often occurs in women age 35 or above. More frequently, it occurs in postmenopausal women (Ilich and Kerstetter, 2000; Ilich et al., 2003).

Dietary supplement with calcium was thought to be the prime factor in the maintenance of bone health in the past 50 years (Seelig et al., 2004). However, the benefit of increased calcium consumption has not been clearly demonstrated for bone health. Instead, high calcium intake may be linked to higher incidence of cardiovascular disease (Seelig et al., 2004). Increased risk of cardiovascular disease was also attributed to a continued increase in calcium to magnesium ratio (Ca/Mg) in the diet. The ratio of Ca/Mg increased from 2/1 in the first 40 years of the 1900 to >3/1 in the sixties, to >6/1 in 2000. The daily recommended intake (DRI) in 2000 was >3/1 to >4/1.

There are conflicting reports in the literature concerning the importance of dietary calcium on bone health. Heaney (1993b; Heaney, 1993a) reviewed 43 studies of calcium published between 1988 and 1993. Although 16 studies showed that calcium had no effect on bone loss, 16 of the 19 placebo-controlled studies in which calcium intake was controlled did show that the mineral prevented or slowed bone loss.

In the 12 studies that excluded women who were within 5 years of menopause, a period when estrogen deficiency overwhelms the effect of calcium supplementation (Riis et al., 1987), all showed that calcium had a significant beneficial effect.

In elderly women, it was shown that there was a significant relationship between bone mineral density (BMD) and several critical nutrients: energy, protein, calcium, magnesium, zinc and vitamin C (Ilich et al., 2003).

In the early 2000, daily calcium intake reached a new high of 2,500 mg (Seelig et al., 2004). It should be noted that the increase in Ca/Mg is mainly due to the increase in calcium intake, not a change in magnesium. The daily requirement of calcium was recently re-evaluated (Hunt and Johnson, 2007). It was found that an average intake of 749 mg of calcium is required, an estimate lower than previously estimated.

In one clinical trial, 43 early postmenopausal women were randomly assigned to one of the treatment groups: percutaneous estradiol, oral calcium (2000 mg/day) or placebo. Bone mineral content in the forearm, the entire body and spine remained the same in the estradiol group; however, there was a decline in the calcium and placebo groups. Calcium did not show any significant effect and calcium supplementation may have a minor effect on the loss of cortical bone, but it had no effect on the trabecular bone (Riis et al., 1987).

In a National Health and Nutritional Examination Survey (NHANES) conducted from 1988 to 1994, predictive models were established to evaluate parameters such as race, body composition, exercise, alcohol intake, smoking status and nutritional intake (Bass et al., 2006). Nutritional intake includes elements such as calcium, phosphorus, magnesium, iron, zinc, sodium and potassium. Among the 7,532 women, 20 years or older, elemental intake was not a predictor of osteoporosis. This observation may not be surprising because the average calcium intake was 659 mg and magnesium was 241 mg. These values were lower than that of RDA of 1000 and 310 mg, respectively.

Physical activity was associated with increase in vertebral bone mineral density (Kanders et al., 1988). When activity was removed, vertebral bone mineral density was dependent on calcium intake. The relationship disappeared when calcium intake exceeded 800 to 1000 mg/day. A ceiling effect of calcium was also observed by Celotti and Bignamini (1999). They reported that calcium supplementation is important for maintaining bone health. However, an excessive amount of calcium may be useless and could cause hypercalciuria and kidney stones. Supplementation with a small amount of magnesium was suggested.

Mutlu et al. (2007) showed that magnesium and zinc levels are the lowest in postmenopausal women, lower than post-menopausal women with osteopenia, and lower than post-menopausal women with normal bone density. Calcium supplementation may reduce zinc absorption, and magnesium and zinc retention. These conditions further aggravate the severity of osteoporosis (Ilich and Kerstetter, 2000; Lowe et al., 2002; Abrams and Atkinson, 2003). Besides calcium, magnesium, zinc, manganese and copper deficiencies are linked to osteoporosis (Saltman and Strause, 1993).

Angus et al. (1988b) showed that calcium was not a predictor of bone mineral density in pre- and post-menopausal women. Magnesium and iron are predictors of bone mineral density. In this study, about 29% of the post-menopausal women consumed less than 500 mg of calcium per day (Angus et al., 1988a). Other nutrients such as magnesium, etc. are also deficient.

A study emphasizing the benefit of magnesium on postmenopausal women found that a Mg/Ca ratio of 1.2/1 was more effective than that of a ratio of 0.4/1 (Abraham and Grewal, 1990). The study used 500 mg of calcium in the form of calcium citrate and 200 mg of magnesium in the form of magnesium oxide for the 0.4/1 group and 600 mg of magnesium in the form of magnesium oxide in the 1.2/1 group. The study showed that women on the 1.2/1 diet for 6 to 12 months had an average of 11% increase in bone mineral density, whereas, the other group had a non-significant increase of 0.7%.

Magnesium supplementation (250 mg/day) in young women has been shown to have no effects on calcium resorption (Basso et al., 2000). This study was a short term study. Therefore, the validity of the results is yet to be confirmed.

Ilich (2000) wrote, "Osteoporosis is a complex, multi-factorial condition characterized by reduced bone mass and impaired micro-architectural structure, leading to an increased susceptibility to fractures. Although most of the bone strength (including bone mass and quality) is genetically determined, many other factors (nutritional, environmental and life-style) also influence bone. Nutrition is an important modifiable factor in the development and maintenance of bone mass and the prevention and treatment of osteoporosis. Approximately 80-90% of bone mineral content is comprised of calcium and phosphorus. Other dietary components, such as protein, magnesium, zinc, copper, iron, fluoride, vitamins D, A, C, and K are required for normal bone metabolism, while other ingested compounds not usually categorized as nutrients (e.g. caffeine, alcohol, phytoestrogens) may also impact on bone health. Unraveling the interaction between different factors; nutritional, environmental, life style, and heredity help us to understand the complexity of the development of osteoporosis and subsequent fractures. This paper reviews the role of dietary components on bone health throughout different stages of life. Each nutrient is discussed separately; however the fact that many nutrients are co-dependent and simultaneously interact with genetic and environmental factors should not be neglected. The complexity of the interactions is probably the reason why there are controversial or inconsistent findings regarding the contribution of a single or a group of nutrients in bone health."

Although bone health is dependent on a variety of factors, there is enough evidence to show that, in the area of elemental requirements, apart from calcium, other elements such as magnesium, phosphorus, zinc, copper, etc. are also important for maintaining or improving bone health.

Despite the values cited in the Recommended Daily Allowance (RDA), Allowable Intake (AI) or Recommended Daily Intake (RDI) for elemental intake, there was not much attention paid to the form of elements consumed. It is not clear whether calcium salts can be used interchangeably. It is understandable that not all calcium salts are created alike; there are differences in solubility and absorption. If there are differences in bioavailability, shouldn't elemental salts be more accurately characterized in terms of absorbability?

These issues have not received appropriate attention because there are reports showing solubility of calcium salts is not related to the element's bioavailability. The absorption of calcium salt, soluble or insoluble, is not affected by gastric acid secretion (Bo-Linn et al., 1984). The hypothesis that calcium carbonate can be converted to a more soluble calcium salt, calcium chloride in the stomach, which enhances calcium absorption has been tested. The results showed that calcium carbonate absorption is not influenced by gastric acid (Bo-Linn et al., 1984). The amount absorbed in humans is 24%.

The bioavailability of calcium carbonate, D-calcium lactate, L-calcium lactate and oyster shell calcium was found to be independent of the salt's solubility (Tsugawa et al., 1995). This study used a method which was different from that of the balance study. It measured changes in the pituitary thyroid hormone (PTH), etc. instead of actual calcium absorption. Accurate comparison of calcium bioavailability cannot be achieved using an indirect method such as PTH.

Heaney (2001) reported that rates of urinary excretion for three marketed calcium products (marketed calcium carbonate, encapsulated calcium carbonate and marketed calcium citrate) were identical. Using $Ca^{45}$ as a tracer, fractional absorption values of calcium carbonate and calcium citrate were found to be insignificantly different from each other at a low dose (300 mg calcium); however, calcium absorption from calcium carbonate was slightly but significantly better than calcium citrate (Heaney et al., 1999).

Magnesium absorption from 10 organic and inorganic salts was tested in rats (Coudray et al., 2005). The bioavailability of magnesium ranged from 50 to 66%. Magnesium gluconate provided the highest value. Solubility of these salts in the small and large intestine and cecum was measured. Solubility of these salts is actually quite high at the proximal section of the intestine; it dropped off very quickly as pH increase along the intestinal tract. Differences in absorption of these magnesium salts may not be important considering the variability among individuals.

Bioavailability of elements in fortified foods has been measured using dual isotope techniques (Abrams et al., 2002). There was no difference in the bioavailability of zinc oxide and zinc sulfate; both are at approximately 24%. The bioavailability of iron was 15.9%. However, zinc sulfate tended to reduce the bioavailability of iron to 11.5% and this number is significant. The absorption of calcium in fortified cereal was 28.9%; in unfortified cereal was 30.8%.

Despite these observations, there are reports showing that not all calcium salts have the same bioavailability.

Bioavailability of calcium ascorbate is higher than that of calcium carbonate and calcium chloride (Tsugawa et al., 1999). The bioavailability was measured using $^{45}Ca$. Solubility of these salts under different pH conditions was also measured.

Bioavailability of calcium acetate was measured using $^{45}Ca$ (Cai et al., 2004). Compared to calcium ascorbate, bioavailability of calcium acetate was significantly lower (70% vs 45% at 25 mg calcium load). A kinetic model consisting of 8 compartments was used to fit the plasma calcium vs. time data. The difference was attributed to a saturable process. It is also reasoned that the solubility of calcium acetate may be reduced in the intestine because calcium from the acetate salt may precipitate phosphate or chloride ions in the intestine.

Therefore, it is not surprising that the bioavailability of calcium acetate is not different from that of calcium chloride and calcium phosphate.

Ten mg of zinc per day is the recommended intake (Record et al., 1985). The recommended daily allowance of zinc was 6 mg (Smith et al., 1983). The authors warned that recommended daily allowance should not be confused with that of recommended daily intake.

Zinc absorption occurs throughout the small intestine and it is dose dependent in humans (Lee et al., 1989).

A patent was filed in 1999 for a calcium dietary supplement comprising calcium, magnesium, zinc, etc. (Ellenbogen and Buono, 1999). The calcium to magnesium ratio is really high and the range of magnesium used was between 50 to 150 mg. The salt for calcium is calcium carbonate. The quantity of calcium and magnesium used and the type of salts employed are different from the present invention.

Meigant and Stenger (2004) filed a U.S. patent citing the a composition which consists of calcium and a vitamin D mixture. It is mentioned that synergism was involved. The thrust of the present application shares no common ground with the application of Meigant and Stenger (2004).

Hendricks (2004) was awarded a patent on a dietary supplement containing calcium and phosphorus. Vitamins including vitamin D could also be included in the supplement. Hendricks emphasized the effects of phosphorus, and perhaps vitamins. The present application, however, does not include phosphorus.

Mazer et al. (1997) was granted a patent on a calcium supplement in solid form which contains calcium glycerophosphate, vitamin D and vitamin C. Again, the present invention does not contain calcium salt of this kind.

In another patent, the synthesis of dicalcium citrate-lactate was described by mixing stoichiometric mixtures of citrate and lactate salts to produce the calcium salt (Walsdorf et al., 1991).

Krumhar and Johnson (2006) designed a diet supplement for bone health consisting of microcrystalline calcium hydroxyapatite, protein (mostly collagen), phosphorus, fat, and other minerals. It also contains vitamin $D_3$, cholecalciferol, and a preferred osteoblast stimulant, ipriflavone. In addition to these basic ingredients, the composition can further include various other minerals known to occur in bone, vitamin C, and glucosamine sulfate, all of which have been claimed to have beneficial effects on the growth and maintenance of healthy bone. A method for benefiting human bone health involves administering a daily regimen of the dietary supplement.

There is another daily vitamin and mineral supplement for women comprising vitamin A, beta-carotene, niacin, riboflavin, pantothenic acid, pyridoxine, cyanocobalamin, biotin, para-aminobenzoic acid, inositol, choline, vitamin C, vitamin D, vitamin E, vitamin K, boron, calcium, chromium, copper, iodine, iron, magnesium, manganese, molybdenum, selenium, zinc and bioflavonoid. For women up to 40 years of age, iron is included. For women over 40 years of age, iron is optionally included (Sultenfuss, 1996). Ca/Mg ratio is 1000-1500/400-600.

A dietary supplement consisting of an extensive list of minerals and vitamins was described in a patent (Jackson and Blumberg, 1997). There is no quantitative description on the contribution of each component to bone health. The focus of this prior patent is distinctly different from the present invention.

Much attention has been focused on calcium as the element for bone health. However, not all calciums are the same and their relative bioavailability determines the fractional amount that reaches the systemic circulation. As for maintenance of bone health, other essential elements are required. There are hints in the literature suggesting that potential interactions between these elements exist. The impact on absorption, calcium utilization and consequently, bone health has not been systematically investigated. Furthermore, vitamins such as $D_3$ and $K_2$ have been implicated in calcium absorption and increase in bone mineral density (BMD); however, the interplay between bioavailable elements, such as calcium, magnesium and zinc, with vitamins has not been illustrated. The complicated environment in the gastrointestinal tract plays a dominant role in determining the absorbability of elements. In particular, cations and anions may play a significant role in altering the solubility of an elemental salt in the gastrointestinal tract (GIT). The importance of these factors in determining the bioavailability of elements has never been thoroughly addressed. In this invention, a calcium supplement, comprising optimum amounts of acetate salts of calcium, magnesium and zinc, and vitamin $D_3$, is described. The daily dosage of calcium is significantly lower than that of regular calcium supplement. This product was designed using in vitro and in vivo models which are key to determining elemental balance.

SUMMARY OF THE INVENTION

The present invention provides a dietary supplement comprising acetate salts of calcium, magnesium, zinc and vitamin $D_3$. This preparation is highly soluble in water, gastric and intestinal fluids. It is also shown that elemental absorption is high and the dosage required for bone health maintenance is approximately a quarter to a third of that of the conventional calcium dose.

DETAILED DESCRIPTION OF THE FIGURES

FIG. 5 shows the plasma calcium (A), magnesium (B) and zinc (C) levels sampled from rats at the end of the treatment period while receiving calcium free diet.

DETAILED DESCRIPTION OF THE INVENTION

Figure 1:
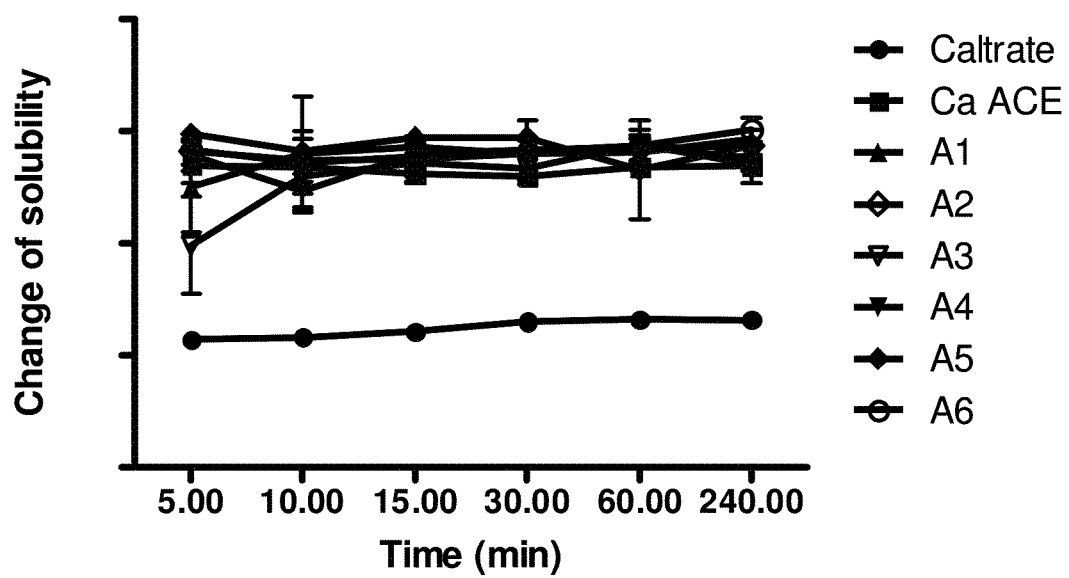
FIG. 1 shows mean (±S.D.) percentage-time profiles of calcium of various formulas in artificial gastric juice (USP).

The following terms shall be used to describe the present invention. In the absence of a specific definition set forth herein, the terms used to describe the present invention shall be given their common meaning as understood by those of ordinary skill in the art.

As used herein, the expression in vivo refers to in the living organism.

As used herein, the expression in vitro refers to in an artificial environment outside the living organism.

As used herein, the expression RDA refers to recommended daily allowance.

As used herein, the expression RDI refers to recommended daily intake

As used herein, the expression AI refers to adequate intake.

As used herein, the expression juice composition refers to a composition comprising juice from fruit, fruit drink, a natural juice, or an artificial juice.

The present invention describes a supplement comprising acetate salts of calcium, magnesium, zinc and vitamin $D_3$.

In one embodiment, the composition of the present invention comprises a weight ratio of calcium to magnesium of 2 or 1. For example, the composition of the present invention may comprise 220 mg of calcium and 110 mg or 220 mg of magnesium. In another embodiment, the composition of the present invention comprises a weight ratio of zinc to calcium ranging from about 0.05 to about 0.1.

The composition of the present invention may comprise a daily dose of 10 to 40 mg of zinc, and/or a daily dose of 400 to 1200 IU of vitamin $D_3$. For example, the composition may comprise 400 to 1200 IU of vitamin $D_3$ per 100-300 mg of calcium.

The composition of the present invention may comprise a daily dose of vitamin $D_3$ of at least 1200 to 3000 IU.

In another embodiment, the composition of the present invention may comprise a daily dose of vitamin $D_3$ is 4000 IU.

In a further embodiment, the composition of the present invention may comprise a daily dose of vitamin $D_3$ is 5000 IU.

In still another embodiment, the composition of the present invention may comprise a daily dose of vitamin $D_3$ is 6000 IU.

In still another embodiment, the composition of the present invention may comprise a daily dose of vitamin $D_3$ is 10,000 IU.

In one embodiment, the present invention provides a composition comprising calcium or synthetic calcium in the form of acetate salt, wherein the composition is further fortified with magnesium, zinc and vitamin D3. In one embodiment, the composition before fortification is an extract from pearl, coral, oyster, or natural mines.

In one embodiment, the present composition comprises magnesium in the form of acetate salt. In another embodiment, the composition comprises zinc in the form of acetate salt.

In an embodiment, the source of magnesium is Synthetic.

In another embodiment, the source of magnesium, is an extract from other magnesium compounds such as magnesium oxide.

In one embodiment, the weight ratio of calcium to magnesium in the present composition can be 0.5:1, 1:1, or 2:1. In another embodiment, the weight ratio of zinc to calcium can range from about 0.05:1 to about 0.20:1.

In one embodiment, the present composition comprises a daily dose of 10-40 mg of zinc. In another embodiment, the composition comprises a daily dose of 400 to 1200 IU of vitamin $D_3$. In yet another embodiment, the composition comprises 100 to 300 mg of calcium and 50 to 150 mg of magnesium, or the composition comprises 400 to 1200 IU of vitamin D3 per 100 to 300 mg of calcium.

In one embodiment, the present composition is more soluble at pH 7 than calcium acetate.

In one embodiment, the present composition comprises more bioavailable calcium per unit weight than calcium carbonate. For example, the present composition may comprise at least 11 percent by weight of calcium in the form of calcium acetate, at least 5 percent by weight of magnesium in the form of magnesium acetate, at least 0.5 percent by weight of zinc in the form of zinc acetate, and at least 400 IU of vitamin D3. In another embodiment, the composition may comprise at least 7 percent by weight of calcium in the form of calcium acetate, at least 7 percent by weight of magnesium in the form of magnesium acetate, at least 0.3 percent by weight of zinc in the form of zinc acetate, and at least 400 IU of vitamin D3.

The present invention also provides a use of the composition disclosed herein for the preparation of medicament for alleviating or treating symptoms of osteoporosis. In one embodiment, the composition comprises between 100 to 300 mg of calcium.

The present invention also provides a juice composition comprising a composition comprising at least 11 percent by weight of calcium in the form of calcium acetate, at least 5 percent by weight of magnesium in the form of magnesium acetate, at least 0.5 percent by weight of zinc in the form of zinc acetate, and at least 400 IU of vitamin $D_3$, wherein said composition comprises more bioavailable calcium per unit weight than calcium carbonate or calcium citrate.

The present invention also provides a juice composition comprising composition comprising at least 7 percent by weight of calcium in the form of calcium acetate, at least 7 percent by weight of magnesium in the form of magnesium acetate, at least 0.3 percent by weight of zinc in the form of zinc acetate, and at least 400 IU of vitamin $D_3$, wherein said composition comprises more bioavailable calcium per unit weight than calcium carbonate or calcium citrate.

The present invention also provides a juice composition comprising the compositions described above.

The present invention also provides a use of the composition disclosed herein for the preparation of medicament for increasing bone mineral density. In one embodiment, the composition comprises between 100 to 300 mg of calcium.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

EXAMPLE 1

Formulations of Pearl Extracts

A pearl extract was prepared by adapting the patented method reported by Li and Li (1995). Briefly, pearls are pulverized to a size between 80 to 120 mesh. The powder is soaked in a mixture of saturated sodium chloride solution with titrated amount of acetic acid. Electrical current is applied to the mixture for several days. After dilution with water and magnetization, the mixture was filtered and precipitated. The precipitate, rich in calcium acetate, is dried and ready for consumption as a dietary supplement. A detailed list of elements present in the extract is presented on Table 1:

TABLE 1

| Content of Pearl Extract | |
|---|---|
| Element | Quantity, ppm |
| Calcium | 233,000 |
| Magnesium | 253 |
| Zinc | 3281 |
| Potassium | 1650 |
| Manganese | 1170 |
| Sodium | 680 |
| Strontium | 158 |
| Molybdenum | 55.4 |
| Silicon | 38.0 |
| Selenium | 27.9 |

This extract, A1, is fortified with acetate salts of magnesium to provide Ca/Mg ratios of 0.5/1 (A6), 1/1 (A4) and 2/1 (A5). The major elemental content of the pearl extract and its fortified mixtures are listed on Table 2:

TABLE 2

The Content of Each Element in Each Formula (n = 3)

The content of three elements in each formula

| Formula No. | Ca (%) | | Mg (%) | | Zn (%) | |
|---|---|---|---|---|---|---|
| | Determined | Labeled content[a] | Determined | Labeled content[a] | Determined | Labeled content[a] |
| A1 | 23.30 ± 1.26 | 23.4 | 0.0253 ± 0.0013 | 0.0012*** | 0.328 ± 0.03 | 0.330 |
| A4 | 7.65 ± 0.62 | 7.51 | 7.56 ± 0.32 | 7.50 | 0.372 ± 0.029 | 0.375 |
| A5 | 11.5 ± 0.34 | 11.3 | 5.41 ± 0.04 | 5.64 | 0.556 ± 0.044 | 0.565 |
| A6 | 4.58 ± 0.09 | 4.50 | 8.29 ± 0.15 | 8.99 | 0.256 ± 0.012 | 0.225 |

Data are expressed as mean ± S.D.
[a]In-house Data.
***$p < 0.001$

Besides Pearl, the method described in this example can also be used to extract multiple acetate salts of calcium, magnesium and zinc from natural sources such as corals, oysters, mineral mines, etc. The composition of formulas A1, A4 through A6 could also be achieved by mixing appropriate amounts of acetates salts of calcium, magnesium and zinc.

EXAMPLE 2

Solubility of Calcium in Artificial Gastric and Intestinal Juice

The solubility of calcium in the four formulas in an artificial gastric (pH=1) and intestinal fluid (pH=7) was tested using a method developed for ICP-OES (Inductively Coupled Plasma Optical Emission Spectrometer) (PerkinElmer Optima 4300DV). Two commercial samples, Caltrate™ and calcium acetate, were also tested in parallel for comparison. The results are shown in Table 3.

Compared to Caltrate™, the solubility of calcium acetate is approximately 45 times higher in the artificial gastric juice and 26,000 times higher in the artificial intestinal juice. The solubility of the pearl extract, A1, comprising mostly calcium acetate, is similar to that of calcium acetate in the artificial gastric juice and intestinal juice (p>0.05). The solubility of calcium acetate is pH dependent; it is lower in the artificial intestinal fluid when compared to the artificial gastric juice. Magnesium has a tendency to lower the solubility of calcium. When the ratio of Ca/Mg decreases, the solubility of the extract decreases, A5>A4>A6. Nevertheless, A6, the least soluble pearl extract formula, is ~12 times more soluble in artificial gastric juice and 8,500 times more soluble in artificial intestinal juice than that of Caltrate™. Therefore, unlike Caltrate™, solubility of acetate salts should not be an issue in GIT fluids.

The solubility profile of magnesium salts is very similar to that of calcium (Table 4). In general, acetate salts of magnesium are highly soluble. They are more soluble in artificial gastric juice than artificial intestinal juice. The solubility of magnesium carbonate in Caltrate™ is low. The carbonate is more soluble in artificial gastric juice as opposed to artificial intestinal juice.

The solubility profile of zinc salts is also similar to that of magnesium and calcium, except the magnitude of difference between salt forms and environmental conditions is less drastic (Table 5).

TABLE 3

Saturated Solubility of Calcium in Artificial Gastric And Intestinal Fluid (n = 3)

| | Saturated solubility of calcium | |
|---|---|---|
| Formula No. | Gastric fluid (g/L) | Intestinal fluid (g/L) |
| A1 | 72.93 ± 4.14 | 64.97 ± 6.29 |
| A4 | 33.60 ± 1.18 | 29.90 ± 2.14 |
| A5 | 53.97 ± 8.34 | 45.50 ± 7.24 |
| A6 | 19.87 ± 3.11 | 20.90 ± 2.36 |
| Calcium Acetate | 77.73 ± 8.13 | 68.43 ± 2.55 |
| Caltrate ™ | 1.70 ± 0.24 | 0.00246 ± 0.00015 |

Data are expressed as Mean ± S.D.

TABLE 4

Saturated Solubility Of Magnesium In Artificial Gastric Fluid And Intestinal Fluid

| | Saturated solubility of magnesium | |
|---|---|---|
| Formula No. | Gastric fluid (g/L) | Intestinal fluid (g/L) |
| A1 | 0.13 ± 0.006 | 0.13 ± 0.04 |
| A2 | 0.11 ± 0.01 | 0.10 ± 0.03 |
| A3 | 0.12 ± 0.04 | 0.09 ± 0.01 |
| A4 | 40.78 ± 2.46 | 26.57 ± 1.81*** |
| A5 | 24.97 ± 2.95 | 19.03 ± 2.73*** |
| A6 | 49.30 ± 2.61 | 38.67 ± 4.33*** |
| Calcium Acetate | 0.50 ± 0.07 | 0.42 ± 0.10 |
| Caltrate ™ | 0.17 ± 0.17 | 0.09 ± 0.02 |

Data are expressed as mean ± S.D. (n = 3).
***$P < 0.001$ compared with solubility in the artificial gastric fluid.

TABLE 5

Saturated Solubility Of Zinc In Artificial Gastric Fluid And Intestinal Fluid

| | Saturated solubility of zinc | |
|---|---|---|
| Formula No. | Gastric fluid (g/L) | Intestinal fluid (g/L) |
| A1 | 1.04 ± 0.16 | 0.76 ± 0.07* |
| A2 | 3.72 ± 0.68 | 2.14 ± 0.14* |
| A3 | 3.25 ± 0.19 | 2.31 ± 0.08** |

TABLE 5-continued

Saturated Solubility Of Zinc In Artificial
Gastric Fluid And Intestinal Fluid

| Formula No. | Saturated solubility of zinc | |
|---|---|---|
| | Gastric fluid (g/L) | Intestinal fluid (g/L) |
| A4 | 2.22 ± 0.17 | 1.19 ± 0.11*** |
| A5 | 2.64 ± 0.38 | 1.64 ± 0.07* |
| A6 | 1.54 ± 0.13 | 1.07 ± 0.11** |
| Calcium Acetate | 0.60 ± 0.17 | 0.53 ± 0.14 |
| Caltrate ™ | 0.33 ± 0.10 | 0.23 ± 0.08 |

Data are expressed as mean ± S.D. (n = 3).
*P < 0.05,
**P < 0.01,
***P < 0.001 compared with the solubility in artificial gastric fluid.

EXAMPLE 3

Effects of pH on the Solubility of Calcium in Different Formulations

The gastrointestinal tract is a complex organ. There are a number of factors which could alter the solubility of elements including calcium, magnesium and zinc; subsequently, their rate of absorption and bioavailability. Examples 3-5 highlight some of the physiological factors which have been postulated to have a significant impact on the solubility of elements. In terms of solubility, the response of the four test formulas (A1, A4, A5 and A6), Caltrate™ and calcium acetate to pH, anions and cations that are present in abundance in GIT fluids was evaluated.

In this example, the effects of pH (ranging from 1 to 9) on the solubility of three elements of the four pearl formulas (A1, A4, A5 and A6), a commercial product (Caltrate™) and a synthetic compound (Calcium Acetate, Ca ACE) were investigated. Solution pH was adjusted using appropriate amounts of acetic acid (AcOH), nitric acid ($HNO_3$) or ammonium hydroxide ($NH_4OH$). Saturated solutions were prepared by dissolving each preparation in a solution with a final pH value ranging from 1 to 9. The resultant mixture was incubated in a water bath at 37° C. for one hour. Each sample was then filtered (with or without centrifugation) immediately, and the filtrate was diluted to an appropriate concentration for elemental analysis. The concentration of calcium, magnesium, and zinc was measured using ICP-OES. The results are shown in Tables 6-8. Statistical analysis was performed using one-way ANOVA and P value was set at 0.05.

Throughout the pH range tested, both A1 and calcium acetate showed significantly higher calcium content in solution than the other preparations. Caltrate™ had the lowest calcium content (p<0.05). A1 and calcium acetate have the highest solubility at pH 1 (Table 6)

Magnesium has a negative effect on the content of calcium in solution; the rank order in terms of solubility is A5>A4>A6. Except for Caltrate™, calcium acetate and A1, which are more soluble at pH 1, pH has no effect on the solubility of magnesium in solution (Table 7).

Similarly, the amount of zinc in solution correlated well with the zinc content in different formulations (A5>A4>A1>A6) (Table 8). For all four acetate formulas tested, pH values higher than 5 were associated with higher solubility than that at pH 2 and 3.

pH may become an issue for calcium absorption when Caltrate™ is administered because intestinal pH values are higher than 6. Under this condition, the solubility of calcium carbonate in Caltrate™ is really low. These results are consistent with that reported on Table 3.

TABLE 6

Calcium Solubility (g/L) In Different pH Solutions (N = 3)

| pH | Caltrate ™ | Ca ACE | A1 | A4 | A5 | A6 |
|---|---|---|---|---|---|---|
| 1 | 4.60 ± 0.28 | 99.0 ± 19.2 | 101 ± 12.9 | 37.6 ± 2.5 | 48.7 ± 2.1 | 23.3 ± 3.2 |
| 2 | 4.04 ± 0.23 | 61.3 ± 0.97 | 64.6 ± 5.1 | 29.4 ± 2.1 | 43.5 ± 5.3 | 22.6 ± 0.54 |
| 3 | 0.507 ± 0.10 | 75.7 ± 4.8 | 71.4 ± 22.2 | 38.0 ± 4.7 | 48.6 ± 0.98 | 19.5 ± 2.5 |
| 4 | 0.237 ± 0.03 | 85.4 ± 5.7 | 75.3 ± 3.4 | 38.5 ± 2.9 | 48.3 ± 0.82 | 20.8 ± 0.98 |
| 5 | 0.240 ± 0.06 | 75.6 ± 5.5 | 65.4 ± 11.8 | 39.3 ± 4.4 | 47.4 ± 8.6 | 24.7 ± 2.5 |
| 6 | 0.317 ± 0.10 | 76.0 ± 5.9 | 83.8 ± 12.7 | 41.2 ± 1.3 | 52.3 ± 5.0 | 19.3 ± 2.7 |
| 7 | 0.133 ± 0.05 | 80.0 ± 3.5 | 84.2 ± 16.8 | 34.6 ± 3.3 | 49.5 ± 8.1 | 20.6 ± 3.8 |
| 8 | 0.160 ± 0.03 | 71.2 ± 1.6 | 78.3 ± 13.0 | 30.0 ± 3.8 | 55.3 ± 7.9 | 19.8 ± 2.0 |
| 9 | 0.227 ± 0.13 | 74.5 ± 6.8 | 84.8 ± 8.2 | 35.8 ± 3.5 | 50.2 ± 1.5 | 19.6 ± 4.2 |

TABLE 7

Magnesium Solubility (g/L) in Different pH Solutions (n = 3)

| pH | Caltrate ™ | Ca ACE | A1 | A4 | A5 | A6 |
|---|---|---|---|---|---|---|
| 1 | 0.197 ± 0.015 | 0.527 ± 0.121 | 0.173 ± 0.015 | 34.697 ± 4.836 | 23.927 ± 1.747 | 41.797 ± 5.622 |
| 2 | 0.100 ± 0.000 | 0.360 ± 0.010 | 0.133 ± 0.006 | 29.117 ± 2.204 | 20.020 ± 2.174 | 39.957 ± 1.050 |
| 3 | 0.133 ± 0.006 | 0.413 ± 0.035 | 0.143 ± 0.021 | 32.640 ± 41.65 | 21.880 ± 0.849 | 34.100 ± 5.169 |
| 4 | 0.123 ± 0.012 | 0.490 ± 0.040 | 0.173 ± 0.015 | 33.560 ± 2.606 | 21.733 ± 0.248 | 34.153 ± 1.560 |
| 5 | 0.107 ± 0.012 | 0.500 ± 0.040 | 0.137 ± 0.012 | 34.510 ± 2.817 | 24.367 ± 3.916 | 45.353 ± 7.294 |
| 6 | 0.110 ± 0.010 | 0.473 ± 0.076 | 0.177 ± 0.040 | 35.747 ± 1.738 | 24.997 ± 0.817 | 34.477 ± 4.730 |
| 7 | 0.093 ± 0.006 | 0.460 ± 0.035 | 0.153 ± 0.015 | 30.197 ± 2.818 | 21.677 ± 3.127 | 36.983 ± 7.234 |
| 8 | 0.097 ± 0.006 | 0.433 ± 0.040 | 0.157 ± 0.015 | 31.023 ± 6.548 | 24.953 ± 3.410 | 34.480 ± 4.046 |
| 9 | 0.097 ± 0.006 | 0.433 ± 0.045 | 0.160 ± 0.010 | 33.473 ± 7.169 | 23.607 ± 1.055 | 34.410 ± 6.836 |

TABLE 8

Zinc Solubility (g/L) in Different pH Solutions (n = 3)

| pH | Caltrate ™ | Ca ACE | A1 | A4 | A5 | A6 |
|---|---|---|---|---|---|---|
| 1 | 0.007 ± 0.006 | 0.030 ± 0.010 | 1.283 ± 0.220 | 1.980 ± 0.256 | 2.637 ± 0.143 | 1.440 ± 0.140 |
| 2 | 0.003 ± 0.006 | 0.013 ± 0.006 | 0.793 ± 0.093 | 1.457 ± 0.032 | 2.220 ± 0.204 | 1.143 ± 0.025 |
| 3 | 0.000 ± 0.000 | 0.017 ± 0.006 | 0.843 ± 0.315 | 1.593 ± 0.216 | 2.103 ± 0.134 | 0.817 ± 0.064 |
| 4 | 0.000 ± 0.000 | 0.017 ± 0.006 | 1.137 ± 0.092 | 1.867 ± 0.078 | 2.383 ± 0.071 | 0.933 ± 0.032 |
| 5 | 0.003 ± 0.006 | 0.017 ± 0.006 | 0.993 ± 0.195 | 1.930 ± 0.164 | 2.790 ± 0.305 | 1.250 ± 0.193 |
| 6 | 0.000 ± 0.000 | 0.020 ± 0.000 | 1.227 ± 0.133 | 2.063 ± 0.059 | 2.837 ± 0.135 | 0.870 ± 0.096 |
| 7 | 0.007 ± 0.012 | 0.023 ± 0.006 | 1.237 ± 0.223 | 1.770 ± 0.132 | 2.493 ± 0.372 | 0.990 ± 0.157 |
| 8 | 0.003 ± 0.006 | 0.027 ± 0.012 | 1.180 ± 0.180 | 1.787 ± 0.306 | 2.903 ± 0.300 | 0.940 ± 0.082 |
| 9 | 0.007 ± 0.006 | 0.027 ± 0.006 | 1.260 ± 0.087 | 1.970 ± 0.364 | 2.753 ± 0.133 | 0.917 ± 0.152 |

EXAMPLE 4

Effects of Anions on the Solubility of Calcium, Magnesium and Zinc in the Test Preparations In this example, the effects of bicarbonate and phosphate ($HCO_3^-$ and $PO_4^{3-}$) on the solubility of calcium, magnesium, and zinc were studied at pH 7. Furthermore, the effects of chloride on the absorption of these three elements at pH 1 and pH 7 were also studied. The procedures described in Example 3 for pH adjustment and solubility measurements were used. ICP-OES was used to quantify calcium, magnesium and zinc. Statistical analysis was performed using one-way ANOVA and the level of significance was set at $p<0.05$.

A. Chloride Effects at pH 1

Tables 9-11 are the results of chloride effects at pH 1. This condition mimics that of the acidic environment in the stomach. Chloride has the most intense effect on the solubility of calcium, magnesium and zinc in Caltrate™ at pH 1 (Tables 9-11). At a $Cl^-$ concentration of 200 mM, the solubility of calcium was the highest. The maximum magnesium and zinc solubility was reached at $Cl^-$ concentrations of 50 mM and 120 mM, respectively. The fluctuations of calcium, magnesium and zinc solubility are minimal in all the acetate formulations: calcium acetate, A1, A4, A5 and A6. Significant differences are often obtained at the highest $Cl^-$ concentration ($p<0.05$).

TABLE 9

The Effect of $Cl^-$ Concentration On The Solubility Of Calcium (g/L) In Different Formulations At pH 1

| Cl⁻ Conc. | Caltrate ™ | Ca ACE | A1 | A4 | A5 | A6 |
|---|---|---|---|---|---|---|
| 0 mM | 4.597 ± 0.276 | 98.950 ± 19.224 | 101.353 ± 12.947 | 37.637 ± 2.509 | 48.670 ± 2.102 | 23.337 ± 3.162 |
| 50 mM | 8.160 ± 0.497 | 80.857 ± 10.277 | 73.950 ± 0.987 | 29.950 ± 6.933 | 42.413 ± 12.931 | 22.290 ± 4.543 |
| 100 mM | 7.333 ± 1.572 | 71.060 ± 1.660 | 85.627 ± 14.191 | 30.023 ± 4.042 | 43.853 ± 2.264 | 24.690 ± 0.746 |
| 120 mM | 8.157 ± 1.210 | 76.453 ± 6.196 | 83.967 ± 0.479 | 36.883 ± 1.966 | 50.283 ± 2.977 | 24.850 ± 1.077 |
| 150 mM | 5.883 ± 1.416 | 73.353 ± 1.037 | 87.340 ± 3.166 | 39.657 ± 4.659 | 44.443 ± 5.495 | 24.647 ± 0.775 |
| 180 mM | 9.073 ± 0.325 | 80.977 ± 12.440 | 88.593 ± 5.579 | 41.710 ± 2.836 | 50.343 ± 1.392 | 26.067 ± 1.891 |
| 200 mM | 12.123 ± 1.178 | 77.257 ± 12.364 | 97.840 ± 12.364 | 42.313 ± 6.119 | 63.027 ± 3.406 | 29.387 ± 4.062 |

TABLE 10

The Effect of $Cl^-$ Concentration On The Solubility Of Magnesium (g/L) In Different Formulations At pH 1

| Cl⁻ Conc. | Caltrate ™ | Ca ACE | A1 | A4 | A5 | A6 |
|---|---|---|---|---|---|---|
| 0 mM | 0.197 ± 0.015 | 0.527 ± 0.121 | 0.173 ± 0.015 | 34.697 ± 4.836 | 23.927 ± 1.747 | 41.797 ± 5.622 |
| 50 mM | 0.357 ± 0.471 | 0.440 ± 0.075 | 0.133 ± 0.006 | 31.420 ± 6.649 | 20.547 ± 6.525 | 45.827 ± 6.006 |
| 100 mM | 0.113 ± 0.012 | 0.380 ± 0.020 | 0.157 ± 0.012 | 35.853 ± 4.215 | 22.697 ± 1.231 | 46.900 ± 4.117 |
| 120 mM | 0.243 ± 0.163 | 0.420 ± 0.036 | 0.140 ± 0.017 | 33.363 ± 2.542 | 23.333 ± 3.312 | 48.827 ± 4.095 |
| 150 mM | 0.220 ± 0.132 | 0.403 ± 0.012 | 0.163 ± 0.015 | 36.037 ± 4.510 | 21.967 ± 1.260 | 45.653 ± 2.449 |
| 180 mM | 0.227 ± 0.134 | 0.420 ± 0.040 | 0.160 ± 0.020 | 38.117 ± 3.356 | 24.210 ± 0.698 | 46.070 ± 3.290 |
| 200 mM | 0.207 ± 0.074 | 0.427 ± 0.080 | 0.163 ± 0.006 | 43.203 ± 4.646 | 29.410 ± 0.115 | 81.437 ± 4.319 |

TABLE 11

The Effect of Cl⁻ Concentration On The Solubility Of Zinc (g/L) In Different Formulations At pH 1

| Cl⁻ Conc. | Caltrate ™ | Ca ACE | A1 | A4 | A5 | A6 |
|---|---|---|---|---|---|---|
| 0 mM | 0.007 ± 0.006 | 0.030 ± 0.010 | 1.283 ± 0.220 | 1.980 ± 0.256 | 2.637 ± 0.143 | 1.440 ± 0.140 |
| 50 mM | 0.030 ± 0.000 | 0.027 ± 0.006 | 0.917 ± 0.156 | 1.500 ± 0.216 | 2.073 ± 0.598 | 1.237 ± 0.110 |
| 100 mM | 0.130 ± 0.026 | 0.067 ± 0.025 | 1.120 ± 0.010 | 1.683 ± 0.100 | 2.353 ± 0.057 | 1.293 ± 0.025 |
| 120 mM | 0.217 ± 0.047 | 0.103 ± 0.031 | 1.113 ± 0.112 | 1.687 ± 0.196 | 2.487 ± 0.273 | 1.363 ± 0.095 |
| 150 mM | 0.277 ± 0.091 | 0.073 ± 0.015 | 1.360 ± 0.144 | 1.803 ± 0.121 | 2.320 ± 0.106 | 1.280 ± 0.046 |
| 180 mM | 0.180 ± 0.060 | 0.117 ± 0.031 | 1.193 ± 0.211 | 1.927 ± 0.015 | 2.590 ± 0.061 | 1.313 ± 0.032 |
| 200 mM | 0.190 ± 0.056 | 0.123 ± 0.040 | 1.413 ± 0.187 | 2.230 ± 0.265 | 3.173 ± 0.248 | 2.083 ± 0.112 |

B. Chloride Effects at pH 7

At pH 7, the solubility of calcium in Caltrate™ is dramatically lower than that at pH 1 in the presence of chloride (Compare values in Tables 9 and 12). As chloride concentration increased, the solubility of calcium in Caltrate™ increased. The pH and chloride effects are not pronounced for the acetate formulations. In general, maximum calcium solubility is reached at chloride concentrations between 50 to 100 mM.

In the presence of chloride, pH has less of an effect on magnesium solubility (compare values between Tables 10 and 13). In general, the solubility of magnesium at pH 7 is slightly lower for all formulas and the chloride effect is not pronounced.

In the presence of chloride, the solubility of zinc in Caltrate™ at pH 7 is less than half of that at pH 1 (compare values between 11 and 14). However, this difference is not pronounced in the acetate formulas. There is a tendency for zinc solubility to increase with the increase of chloride concentration. Maximum zinc solubility is reached at 120 mM chloride when Caltrate™ was evaluated. For the acetate formulas, maximum zinc solubility occurred when chloride concentration reached 200 mM.

TABLE 12

The Effect of Cl⁻ Concentration On The Solubility Of Calcium In Different Formulations At pH 7

| Cl⁻ Conc. | Caltrate ™ [g/L] | Ca ACE [g/L] | A1 [g/L] | A4 [g/L] | A5 [g/L] | A6 [g/L] |
|---|---|---|---|---|---|---|
| 0 mM | 0.133 ± 0.051 | 80.017 ± 3.505 | 84.170 ± 16.834 | 34.640 ± 3.268 | 49.497 ± 8.097 | 20.627 ± 3.821 |
| 50 mM | 0.340 ± 0.082 | 99.373 ± 6.182 | 80.703 ± 13.103 | 47.473 ± 2.381 | 61.537 ± 6.436 | 31.490 ± 2.399 |
| 100 mM | 0.557 ± 0.040 | 87.263 ± 13.984 | 77.660 ± 19.779 | 47.867 ± 7.511 | 66.743 ± 13.191 | 29.053 ± 6.684 |
| 120 mM | 0.370 ± 0.165 | 71.440 ± 5.851 | 61.437 ± 8.616 | 35.400 ± 0.864 | 45.060 ± 6.166 | 22.353 ± 2.351 |
| 150 mM | 0.567 ± 0.075 | 70.923 ± 3.240 | 73.773 ± 12.437 | 33.017 ± 2.455 | 42.980 ± 2.603 | 20.313 ± 2.005 |
| 180 mM | 0.560 ± 0.165 | 77.823 ± 12.314 | 59.720 ± 7.467 | 34.003 ± 0.846 | 42.890 ± 5.516 | 17.490 ± 0.916 |
| 200 mM | 0.600 ± 0.132 | 73.930 ± 7.785 | 84.707 ± 15.685 | 33.223 ± 2.093 | 46.403 ± 4.643 | 18.627 ± 2.238 |

TABLE 13

The Effect of Cl⁻ Concentration On The Solubility Of Magnesium In Different Formulations At pH 7

| Cl⁻ Conc. | Caltrate ™ [g/L] | Ca ACE [g/L] | A1 [g/L] | A4 [g/L] | A5 [g/L] | A6 [g/L] |
|---|---|---|---|---|---|---|
| 0 mM | 0.093 ± 0.006 | 0.460 ± 0.035 | 0.153 ± 0.015 | 30.197 ± 2.818 | 21.677 ± 3.127 | 36.983 ± 7.234 |
| 50 mM | 0.280 ± 0.202 | 0.503 ± 0.031 | 0.140 ± 0.020 | 43.190 ± 2.792 | 29.203 ± 1.107 | 56.003 ± 3.989 |
| 100 mM | 0.280 ± 0.149 | 0.480 ± 0.017 | 0.143 ± 0.006 | 45.253 ± 6.350 | 30.917 ± 6.111 | 52.953 ± 14.721 |
| 120 mM | 0.110 ± 0.026 | 0.390 ± 0.030 | 0.147 ± 0.012 | 31.983 ± 3.302 | 19.333 ± 2.217 | 42.463 ± 1.448 |
| 150 mM | 0.227 ± 0.096 | 1.750 ± 2.382 | 0.167 ± 0.015 | 29.087 ± 0.957 | 19.383 ± 1.482 | 42.643 ± 0.446 |
| 180 mM | 0.253 ± 0.129 | 0.430 ± 0.046 | 0.167 ± 0.006 | 32.633 ± 2.372 | 19.733 ± 2.149 | 36.160 ± 10.009 |
| 200 mM | 0.283 ± 0.107 | 0.427 ± 0.065 | 0.203 ± 0.025 | 32.923 ± 0.802 | 23.067 ± 2.175 | 47.133 ± 1.598 |

TABLE 14

The Effect of Cl⁻ Concentration On The Solubility Of Zinc In Different Formulations At pH 7

| Cl⁻ Conc. | Caltrate ™ [g/L] | Ca ACE [g/L] | A1 [g/L] | A4 [g/L] | A5 [g/L] | A6 [g/L] |
|---|---|---|---|---|---|---|
| 0 mM | 0.007 ± 0.012 | 0.023 ± 0.006 | 1.237 ± 0.223 | 1.770 ± 0.132 | 2.493 ± 0.372 | 0.990 ± 0.157 |
| 50 mM | 0.113 ± 0.006 | 0.180 ± 0.089 | 0.997 ± 0.195 | 2.057 ± 0.189 | 3.177 ± 0.289 | 1.457 ± 0.244 |
| 100 mM | 0.140 ± 0.026 | 0.213 ± 0.102 | 0.903 ± 0.280 | 2.413 ± 0.144 | 3.063 ± 0.287 | 1.540 ± 0.380 |
| 120 mM | 0.050 ± 0.017 | 0.167 ± 0.202 | 0.760 ± 0.118 | 1.573 ± 0.146 | 1.997 ± 0.254 | 1.110 ± 0.036 |
| 150 mM | 0.087 ± 0.025 | 0.177 ± 0.085 | 0.987 ± 0.110 | 2.030 ± 0.615 | 2.010 ± 0.165 | 1.177 ± 0.072 |
| 180 mM | 0.093 ± 0.015 | 0.143 ± 0.071 | 0.780 ± 0.151 | 1.637 ± 0.127 | 2.090 ± 0.167 | 1.077 ± 0.163 |
| 200 mM | 0.093 ± 0.012 | 0.160 ± 0.079 | 1.117 ± 0.202 | 1.663 ± 0.078 | 1.643 ± 1.217 | 1.303 ± 0.060 |

C. Bicarbonate Effects at pH 7.

The solubility of calcium in Caltrate™ increased with the increase of bicarbonate concentration (Table 15). However, the opposite is true for calcium acetate. The solubility was reduced at least 40%. The reduction for all the pearl extract formulas was less, approximately 20 to 25%.

The solubility of magnesium in Caltrate™ increased with bicarbonate concentration (Table 16). Bicarbonate effect was minimal for the acetate formulas.

The solubility of zinc in Caltrate™ increased in the presence of bicarbonate (Table 17). Maximum zinc solubility was reached at 70 mM. For calcium acetate, the trend is similar to that of Caltrate™. Bicarbonate has very little effect on the pearl extract formulas.

tions increased the solubility of calcium decreased in all acetate formulations. Maximum reduction (up to 40%) of the solubility of calcium was observed in formulas containing higher percentage of magnesium (A4, A5 and A6). Considering the range of phosphate concentration tested, 10,000-fold, the change of calcium solubility is not significant.

Magnesium solubility decreased as phosphate concentration increased (Table 19). The reduction (80%) is most significant for the magnesium in Caltrate™. For the other formulas, the maximum reduction was approximately 50%. Again, the effect of phosphates was not that significant considering the range of concentration tested.

Among the three elements, phosphates have the most intense effect on the solubility of zinc (Table 20). All formulas were affected to the same extent and the maximum reduction

TABLE 15

The Effect of $HCO_3^-$ Concentration On The Solubility Of Calcium In Different Formulations At pH 7

| $HCO_3^-$ Conc. | Caltrate™ [g/L] | Ca ACE [g/L] | A1 [g/L] | A4 [g/L] | A5 [g/L] | A6 [g/L] |
|---|---|---|---|---|---|---|
| 0 mM | 0.133 ± 0.051 | 80.017 ± 3.505 | 84.170 ± 16.834 | 34.640 ± 3.268 | 49.497 ± 8.097 | 20.627 ± 3.821 |
| 50 mM | 0.217 ± 0.214 | 50.243 ± 3.312 | 72.030 ± 7.103 | 36.007 ± 3.807 | 42.577 ± 0.779 | 21.737 ± 1.255 |
| 70 mM | 0.213 ± 0.098 | 62.090 ± 8.524 | 70.933 ± 4.812 | 33.420 ± 5.263 | 42.130 ± 4.734 | 22.343 ± 0.847 |
| 100 mM | 0.380 ± 0.075 | 56.367 ± 9.062 | 83.640 ± 10.870 | 34.997 ± 6.049 | 46.167 ± 4.546 | 25.260 ± 10.191 |
| 120 mM | 0.440 ± 0.167 | 46.023 ± 2.463 | 67.010 ± 3.767 | 31.060 ± 2.23 | 46.973 ± 2.919 | 20.817 ± 1.664 |
| 150 mM | 0.433 ± 0.120 | 70.637 ± 3.622 | 65.617 ± 1.475 | 30.410 ± 2.888 | 41.567 ± 4.620 | 19.163 ± 1.568 |
| 180 mM | 0.930 ± 1.290 | 46.847 ± 2.741 | 65.270 ± 1.781 | 28.680 ± 1.362 | 38.073 ± 3.465 | 18.870 ± 1.679 |

TABLE 16

The Effect of $HCO_3^-$ Concentration On The Solubility Of Magnesium In Different Formulations At pH 7

| $HCO_3^-$ Conc. | Caltrate™ [g/L] | Ca ACE [g/L] | A1 [g/L] | A4 [g/L] | A5 [g/L] | A6 [g/L] |
|---|---|---|---|---|---|---|
| 0 mM | 0.093 ± 0.006 | 0.460 ± 0.035 | 0.153 ± 0.015 | 30.197 ± 2.818 | 21.677 ± 3.127 | 36.983 ± 7.234 |
| 50 mM | 0.090 ± 0.035 | 0.297 ± 0.055 | 0.190 ± 0.056 | 34.600 ± 4.638 | 20.427 ± 1.272 | 48.140 ± 1.653 |
| 70 mM | 0.093 ± 0.012 | 0.347 ± 0.031 | 0.160 ± 0.000 | 32.057 ± 4.407 | 22.000 ± 0.141 | 42.767 ± 0.460 |
| 100 mM | 0.223 ± 0.111 | 0.343 ± 0.101 | 0.167 ± 0.065 | 41.580 ± 12.984 | 26.393 ± 4.720 | 43.883 ± 1.288 |
| 120 mM | 0.220 ± 0.069 | 0.303 ± 0.015 | 0.483 ± 0.551 | 30.960 ± 2.164 | 22.877 ± 1.082 | 46.990 ± 5.278 |
| 150 mM | 0.227 ± 0.072 | 0.410 ± 0.061 | 0.150 ± 0.017 | 28.950 ± 2.262 | 18.850 ± 2.169 | 42.877 ± 7.608 |
| 180 mM | 0.240 ± 0.095 | 0.293 ± 0.049 | 0.163 ± 0.015 | 30.787 ± 1.021 | 19.607 ± 1.529 | 36.957 ± 0.839 |

TABLE 17

The Effect of $HCO_3^-$ Concentration On The Solubility Of Zinc In Different Formulations At pH 7

| $HCO_3^-$ Conc. | Caltrate™ [g/L] | Ca ACE [g/L] | A1 [g/L] | A4 [g/L] | A5 [g/L] | A6 [g/L] |
|---|---|---|---|---|---|---|
| 0 mM | 0.007 ± 0.012 | 0.023 ± 0.006 | 1.237 ± 0.223 | 1.770 ± 0.132 | 2.493 ± 0.372 | 0.990 ± 0.157 |
| 50 mM | 0.057 ± 0.015 | 0.050 ± 0.010 | 0.953 ± 0.101 | 1.663 ± 0.205 | 2.010 ± 0.142 | 1.260 ± 0.017 |
| 70 mM | 0.070 ± 0.020 | 0.100 ± 0.061 | 0.990 ± 0.082 | 1.560 ± 0.236 | 2.237 ± 0.099 | 1.147 ± 0.081 |
| 100 mM | 0.070 ± 0.017 | 0.157 ± 0.055 | 1.190 ± 0.101 | 2.067 ± 0.654 | 2.660 ± 0.442 | 1.193 ± 0.023 |
| 120 mM | 0.093 ± 0.025 | 0.210 ± 0.096 | 0.907 ± 0.042 | 1.513 ± 0.127 | 2.290 ± 0.115 | 1.317 ± 0.182 |
| 150 mM | 0.087 ± 0.021 | 0.137 ± 0.083 | 0.863 ± 0.081 | 1.427 ± 0.059 | 1.887 ± 0.144 | 1.237 ± 0.235 |
| 180 mM | 0.070 ± 0.017 | 0.160 ± 0.078 | 0.933 ± 0.072 | 1.517 ± 0.119 | 1.997 ± 0.157 | 1.023 ± 0.042 |

D. Effects of Phosphates at pH 7

Phosphates have insignificant effects on the solubility of calcium in Caltrate™ (Table 18). As phosphate concentrawas approximately 70%. Considering the range of phosphate concentration tested, again, the effects of phosphates were not that significant.

TABLE 18

The Effect of $PO_4^{3-}$ Concentration On The Solubility Of Calcium In Different Formulations At pH 7

| $PO_4^{3-}$ Conc. | Caltrate™ [g/L] | Ca ACE [g/L] | A1 [g/L] | A4 [g/L] | A5 [g/L] | A6 [g/L] |
|---|---|---|---|---|---|---|
| 0.01 mM | 0.587 ± 0.200 | 77.517 ± 6.084 | 84.270 ± 9.511 | 34.950 ± 6.725 | 47.823 ± 3.080 | 22.287 ± 2.539 |
| 1 mM | 0.510 ± 0.252 | 68.220 ± 19.638 | 56.450 ± 9.879 | 39.923 ± 10.060 | 42.363 ± 3.572 | 23.530 ± 0.159 |
| 10 mM | 0.430 ± 0.046 | 78.417 ± 7.046 | 64.697 ± 9.058 | 25.703 ± 7.033 | 41.287 ± 3.584 | 21.687 ± 1.156 |
| 100 mM | 0.453 ± 0.158 | 64.770 ± 1.548 | 58.607 ± 9.415 | 25.090 ± 3.181 | 34.650 ± 6.972 | 15.437 ± 2.428 |

TABLE 19

The Effect of $PO_4^{3-}$ Concentration On The Solubility Of Magnesium In Different Formulations At pH 7

| $PO_4^{3-}$ Conc. | Caltrate™ [g/L] | Ca ACE [g/L] | A1 [g/L] | A4 [g/L] | A5 [g/L] | A6 [g/L] |
|---|---|---|---|---|---|---|
| 0.01 mM | 0.280 ± 0.070 | 0.493 ± 0.025 | 0.203 ± 0.006 | 38.017 ± 2.532 | 24.733 ± 0.886 | 52.000 ± 5647 |
| 1 mM | 0.317 ± 0.087 | 0.450 ± 0.095 | 0.217 ± 0.031 | 35.647 ± 10.790 | 18.583 ± 1.676 | 48.967 ± 1.486 |
| 10 mM | 0.240 ± 0.050 | 0.477 ± 0.035 | 0.173 ± 0.012 | 20.837 ± 5.545 | 18.163 ± 1.368 | 37.140 ± 2.681 |
| 100 mM | 0.073 ± 0.006 | 0.350 ± 0.017 | 0.127 ± 0.012 | 21.490 ± 1.830 | 16.720 ± 4.514 | 31.163 ± 4.838 |

TABLE 20

The Effect of $PO_4^{3-}$ Concentration On The Solubility Of Zinc In Different Formulations At pH 7

| $PO_4^{3-}$ Conc. | Caltrate™ [g/L] | Ca ACE [g/L] | A1 [g/L] | A4 [g/L] | A5 [g/L] | A6 [g/L] |
|---|---|---|---|---|---|---|
| 0.01 mM | 0.117 ± 0.042 | 0.190 ± 0.070 | 1.193 ± 0.097 | 1.950 ± 0.040 | 2.750 ± 0.135 | 1.470 ± 0.154 |
| 1 mM | 0.100 ± 0.044 | 0.197 ± 0.110 | 0.780 ± 0.151 | 1.800 ± 0.394 | 1.993 ± 0.093 | 1.380 ± 0.079 |
| 10 mM | 0.070 ± 0.010 | 0.180 ± 0.089 | 0.767 ± 0.137 | 0.937 ± 0.253 | 1.740 ± 0.173 | 1.023 ± 0.060 |
| 100 mM | 0.033 ± 0.015 | 0.053 ± 0.023 | 0.527 ± 0.119 | 0.623 ± 0.087 | 1.013 ± 0.345 | 0.510 ± 0.131 |

EXAMPLE 5

Effects of Cations on the Solubility of Calcium, Magnesium and Zinc in the Test Preparations A. Effects of $Na^+$ at pH 1

The effects of $Na^+$ concentration on the solubility of the three elements in the four formulations (A1, A4, A5, and A6), Caltrate™ and CaACE were investigated at gastric pH (pH=1) and intestinal pH (pH=7), respectively. Tables 21 and 22 show the results tested at pH 1. No significant effects of $Na^+$ concentration on calcium and magnesium solubility of all formulations were observed. Solubility of zinc in Caltrate™ and calcium acetate, which contained trace amounts of Zn, increased significantly with an increase in sodium concentrations; however, no significant differences were obtained for all the acetate formulations (Table 23).

TABLE 21

Effect Of Concentration Of $Na^+$ On The Solubility Of Calcium Of Each Formula At pH 1

| $Na^+$ Conc. (mM) | Solubility of calcium (g/L) | | | | | |
|---|---|---|---|---|---|---|
| | Caltrate™ | CaACE | A1 | A4 | A5 | A6 |
| 0 | 4.597 ± 0.276 | 98.950 ± 19.224 | 101.353 ± 12.947 | 37.637 ± 2.509 | 48.670 ± 2.102 | 23.337 ± 3.162 |
| 5 | 5.447 ± 2.061 | 84.800 ± 13.912 | 72.233 ± 1.501 | 36.467 ± 5.173 | 46.100 ± 0.721 | 22.000 ± 1.323 |
| 10 | 4.340 ± 0.035 | 66.967 ± 17.377 | 80.000 ± 1.852 | 40.033 ± 4.623 | 49.833 ± 2.503 | 27.900 ± 3.736 |
| 50 | 4.640 ± 0.707 | 90.167 ± 9.343 | 83.467 ± 3.313 | 36.633 ± 1.877 | 49.033 ± 4.452 | 25.467 ± 0.231 |
| 80 | 5.530 ± 0.946 | 87.167 ± 3.630 | 83.067 ± 6.813 | 37.033 ± 1.069 | 55.733 ± 5.372 | 30.600 ± 1.709 |
| 100 | 5.360 ± 0.742 | 79.233 ± 15.964 | 84.900 ± 11.609 | 39.100 ± 5.696 | 48.733 ± 3.968 | 25.067 ± 0.153 |

Data are expressed as mean ± S.D.

No statistical differences in all $Na^+$ concentrations tested for all formulations tested.

TABLE 22

Effect Of Concentration Of $Na^+$ On The Solubility Of Magnesium Of Each Formula At pH 1

| Na+ Conc. (mM) | Solubility of magnesium (g/L) | | | | | |
|---|---|---|---|---|---|---|
| | Caltrate ™ | CaACE | A1 | A4 | A5 | A6 |
| 0 | 0.197 ± 0.015 | 0.527 ± 0.121 | 0.173 ± 0.015 | 34.697 ± 4.836 | 23.927 ± 1.747 | 41.797 ± 5.622 |
| 5 | 0.223 ± 0.006 | 0.700 ± 0.183 | 0.283 ± 0.040 | 36.400 ± 4.854 | 24.467 ± 1.361 | 39.933 ± 1.343 |
| 10 | 1.037 ± 1.109 | 0.483 ± 0.115 | 0.317 ± 0.050 | 38.967 ± 5.745 | 23.900 ± 1.800 | 49.100 ± 3.305 |
| 50 | 0.807 ± 0.889 | 0.620 ± 0.115 | 0.237 ± 0.031 | 35.733 ± 1.909 | 22.667 ± 2.055 | 45.500 ± 2.211 |
| 80 | 1.087 ± 1.264 | 0.580 ± 0.061 | 0.960 ± 1.031 | 35.033 ± 3.625 | 27.767 ± 3.700 | 50.900 ± 7.375 |
| 100 | 0.577 ± 0.525 | 0.497 ± 0.025 | 0.223 ± 0.032 | 36.000 ± 5.629 | 21.267 ± 2.120 | 46.233 ± 1.401 |

Data are expressed as mean ± S.D.
No statistical differences in all $Na^+$ concentrations tested for all formulations tested.

TABLE 23

A Effect Of Concentration Of $Na^+$ On The Solubility Of Zinc Of Each Formula At pH 1

| Na+ Conc. (mM) | Solubility of zinc (g/L) | | | | | |
|---|---|---|---|---|---|---|
| | Caltrate ™ | CaACE | A1 | A4 | A5 | A6 |
| 0 | 0.007 ± 0.006 | 0.030 ± 0.010 | 1.283 ± 0.220 | 1.980 ± 0.256 | 2.637 ± 0.143 | 1.440 ± 0.140 |
| 5 | 0.087 ± 0.006 | 0.123 ± 0.006 | 0.660 ± 0.128 | 1.393 ± 0.316 | 2.180 ± 0.413 | 1.183 ± 0.121 |
| 10 | 0.173 ± 0.015 | 0.317 ± 0.106 | 0.883 ± 0.080 | 1.767 ± 0.280 | 2.080 ± 0.160 | 1.760 ± 0.617 |
| 50 | 0.240 ± 0.053 | 0.400 ± 0.139 | 1.023 ± 0.075 | 1.727 ± 0.060 | 2.250 ± 0.114 | 1.410 ± 0.125 |
| 80 | 0.210 ± 0.026 | 0.397 ± 0.163 | 0.907 ± 0.211 | 1.730 ± 0.479 | 2.613 ± 0.270 | 1.747 ± 0.015 |
| 100 | 0.223 ± 0.031 | 0.363 ± 0.095 | 0.947 ± 0.188 | 1.490 ± 0.105 | 2.207 ± 0.506 | 1.493 ± 0.630 |

Data are expressed as mean ± S.D

B. Effects of $Na^+$ at pH 7

Tables 24-26 show the effects of sodium ion at pH 7. $Na^+$ has no significant effects on calcium, magnesium and zinc solubility in general. It is interesting to note that all three elements in Caltrate™ could be not detected in the presence of $Na^+$ at pH 7.

TABLE 24

Effect Of Concentration Of $Na^+$ On The Solubility Of Calcium Of Each Formula At pH 7

| Na+ Conc. (mM) | Solubility of calcium (g/L) | | | | | |
|---|---|---|---|---|---|---|
| | Caltrate ™ | CaACE | A1 | A4 | A5 | A6 |
| 0 | 0.133 ± 0.051 | 98.950 ± 19.224 | 101.353 ± 12.947 | 37.637 ± 2.509 | 48.670 ± 2.102 | 23.337 ± 3.162 |
| 10 | — | 83.300 ± 26.469 | 67.433 ± 4.460 | 37.433 ± 4.822 | 43.800 ± 4.703 | 39.367 ± 16.110 |
| 50 | — | 69.000 ± 1.015 | 99.333 ± 21.548 | 35.533 ± 0.814 | 48.367 ± 4.359 | 23.833 ± 2.219 |
| 100 | — | 71.467 ± 10.891 | 71.433 ± 1.193 | 36.867 ± 3.139 | 46.267 ± 1.380 | 24.567 ± 4.104 |
| 140 | — | 83.067 ± 6.596 | 68.900 ± 7.400 | 32.300 ± 1.153 | 47.200 ± 6.023 | 25.633 ± 3.754 |
| 170 | — | 72.333 ± 15.467 | 71.433 ± 0.551 | 37.567 ± 10.473 | 43.133 ± 4.876 | 25.867 ± 3.175 |

Data are expressed as mean ± S.D.
No statistical differences in all $Na^+$ concentrations tested for all formulations tested.

TABLE 25

A Effect Of Concentration Of $Na^+$ On The Solubility Of Magnesium Of Each Formula At pH 7

| Na+ Conc.(mM) | Solubility of magnesium (g/L) | | | | | |
|---|---|---|---|---|---|---|
| | Caltrate ™ | CaACE | A1 | A4 | A5 | A6 |
| 0 | 0.093 ± 0.006 | 0.527 ± 0.121 | 0.173 ± 0.015 | 34.697 ± 4.836 | 23.927 ± 1.747 | 41.797 ± 5.622 |
| 10 | — | 0.740 ± 0.165 | 0.110 ± 0.010 | 35.300 ± 3.579 | 19.500 ± 1.769 | 75.167 ± 34.360 |
| 50 | — | 0.427 ± 0.081 | 0.193 ± 0.015 | 35.933 ± 5.139 | 23.000 ± 4.327 | 52.167 ± 4.852 |
| 100 | — | 0.510 ± 0.066 | 0.157 ± 0.006 | 33.267 ± 3.889 | 20.667 ± 0.493 | 45.867 ± 3.329 |

TABLE 25-continued

A Effect Of Concentration Of Na$^+$ On The Solubility Of Magnesium Of Each Formula At pH 7

| Na+ Conc.(mM) | Caltrate ™ | CaACE | A1 | A4 | A5 | A6 |
|---|---|---|---|---|---|---|
| 140 | — | 0.497 ± 0.099 | 0.157 ± 0.021 | 28.867 ± 2.255 | 20.567 ± 2.610 | 51.000 ± 6.963 |
| 170 | — | 0.530 ± 0.036 | 0.167 ± 0.021 | 45.633 ± 11.097 | 21.600 ± 2.476 | 53.500 ± 3.650 |

Data are expressed as mean ± S.D.

TABLE 26

A Effect Of Concentration Of Na$^+$ On The Solubility Of Zinc Of Each Formula At pH 7

| Na+ Conc.(mM) | Caltrate ™ | CaACE | A1 | A4 | A5 | A6 |
|---|---|---|---|---|---|---|
| 0 | 0.007 ± 0.012 | 0.030 ± 0.010 | 1.283 ± 0.220 | 1.980 ± 0.256 | 2.637 ± 0.143 | 1.440 ± 0.140 |
| 10 | — | 0.213 ± 0.102 | 0.600 ± 0.040 | 1.453 ± 0.185 | 1.543 ± 0.215 | 2.337 ± 1.351 |
| 50 | — | 0.280 ± 0.118 | 0.963 ± 0.280 | 1.700 ± 0.779 | 2.317 ± 0.798 | 1.687 ± 0.466 |
| 100 | — | 0.293 ± 0.129 | 0.707 ± 0.107 | 1.243 ± 0.211 | 1.790 ± 0.087 | 1.667 ± 0.275 |
| 140 | — | 0.320 ± 0.165 | 0.690 ± 0.137 | 1.113 ± 0.144 | 1.770 ± 0.056 | 1.643 ± 0.402 |
| 170 | — | 0.223 ± 0.102 | 0.730 ± 0.079 | 2.230 ± 0.397 | 1.933 ± 0.838 | 1.577 ± 0.529 |

Data are expressed as mean ± S.D.

C. Effects of K$^+$ at pH 1

There is a tendency for the solubility of calcium to increase with an increase in potassium ion concentration (Table 27). However, most of the differences are not statistically different (p<0.05). In A5, the calcium solubility increased by more than 50%; this difference is significant (p<0.05).

Magnesium solubility profiles show a similar trend (Table 28) to that of calcium. The most pronounced was that measured for Caltrate™, a three-fold increase (p<0.05). This trend was not significant for all the acetate formulas.

Zinc solubility tended to increase with an increase in potassium concentration (Table 29). The most pronounced increase was obtained from the zinc in Caltrate™. A similar trend was observed for calcium acetate. The trend was insignificant for the pearl extract formulas (p>0.05).

TABLE 27

A Effect Of Concentration Of K$^+$ On The Solubility Of Calcium Of Each Formula At pH 1

| K$^+$ Conc. (mM) | Caltrate ™ | CaACE | A1 | A4 | A5 | A6 |
|---|---|---|---|---|---|---|
| 0 | 4.597 ± 0.276 | 98.950 ± 19.224 | 101.353 ± 12.947 | 37.637 ± 2.509 | 48.670 ± 2.102 | 23.337 ± 3.162 |
| 2 | 4.300 ± 0.403 | 78.933 ± 1.320 | 71.833 ± 9.338 | 34.033 ± 1.739 | 35.833 ± 5.314 | 24.067 ± 1.474 |
| 5 | 3.607 ± 0.540 | 71.033 ± 13.079 | 73.733 ± 3.412 | 36.967 ± 1.159 | 47.500 ± 5.272 | 23.500 ± 1.778 |
| 10 | 6.497 ± 3.381 | 158.333 ± 40.624 | 83.733 ± 14.093 | 40.467 ± 7.823 | 66.567 ± 21.033 | 30.867 ± 10.262 |
| 15 | 6.877 ± 0.956 | 161.667 ± 46.918 | 92.167 ± 14.793 | 41.867 ± 7.019 | 63.333 ± 7.651 | 26.667 ± 0.473 |
| 20 | 3.567 ± 0.501 | 100.800 ± 3.811 | 103.333 ± 15.822 | 42.633 ± 4.674 | 103.567 ± 64.463 | 29.300 ± 3.751 |

Data are expressed as mean ± S.D.

TABLE 28

A Effect Of Concentration Of K$^+$ On The Solubility Of Magnesium Of Each Formula At pH 1

| K$^+$ Conc. (mM) | Caltrate ™ | CaACE | A1 | A4 | A5 | A6 |
|---|---|---|---|---|---|---|
| 0 | 0.197 ± 0.015 | 0.527 ± 0.121 | 0.173 ± 0.015 | 34.697 ± 4.836 | 23.927 ± 1.747 | 41.797 ± 5.622 |
| 2 | 0.223 ± 0.087 | 0.693 ± 0.283 | 0.203 ± 0.029 | 34.933 ± 1.716 | 21.633 ± 4.300 | 49.700 ± 1.249 |
| 5 | 0.490 ± 0.419 | 0.453 ± 0.112 | 0.170 ± 0.030 | 32.667 ± 2.542 | 23.433 ± 3.408 | 43.000 ± 2.406 |
| 10 | 0.703 ± 0.846 | 0.820 ± 0.193 | 0.270 ± 0.130 | 38.733 ± 5.552 | 30.067 ± 8.429 | 55.400 ± 18.187 |

TABLE 28-continued

A Effect Of Concentration Of K⁺ On The Solubility Of Magnesium Of Each Formula At pH 1

| K⁺ Conc. (mM) | Solubility of magnesium (g/L) | | | | | |
|---|---|---|---|---|---|---|
| | Caltrate ™ | CaACE | A1 | A4 | A5 | A6 |
| 15 | 0.730 ± 0.912 | 0.687 ± 0.215 | 0.327 ± 0.185 | 41.467 ± 8.617 | 31.067 ± 4.050 | 54.800 ± 3.897 |
| 20 | 0.660 ± 0.764 | 0.650 ± 0.020 | 0.883 ± 1.140 | 52.067 ± 2.859 | 55.733 ± 34.208 | 54.233 ± 14.632 |

Data are expressed as mean ± S.D.

TABLE 29

A Effect Of Concentration Of K⁺ On The Solubility Of Zinc Of Each Formula At pH 1

| K+ Conc. (mM) | Solubility of zinc (g/L) | | | | | |
|---|---|---|---|---|---|---|
| | Caltrate ™ | CaACE | A1 | A4 | A5 | A6 |
| 0 | 0.007 ± 0.006 | 0.030 ± 0.010 | 1.283 ± 0.220 | 1.980 ± 0.256 | 2.637 ± 0.143 | 1.440 ± 0.140 |
| 2 | 0.053 ± 0.015 | 0.077 ± 0.006 | 0.607 ± 0.108 | 1.377 ± 0.221 | 1.937 ± 0.591 | 1.360 ± 0.122 |
| 5 | 0.173 ± 0.035 | 0.240 ± 0.075 | 0.790 ± 0.147 | 1.297 ± 0.169 | 2.593 ± 0.821 | 1.143 ± 0.278 |
| 10 | 0.203 ± 0.058 | 0.357 ± 0.111 | 1.127 ± 0.142 | 1.630 ± 0.185 | 2.373 ± 0.658 | 1.627 ± 0.225 |
| 15 | 0.193 ± 0.023 | 1.307 ± 1.199 | 1.060 ± 0.600 | 1.953 ± 0.590 | 2.963 ± 0.309 | 1.630 ± 0.161 |
| 20 | 0.167 ± 0.015 | 0.293 ± 0.093 | 1.100 ± 0.140 | 2.500 ± 0.236 | 5.450 ± 3.159 | 2.540 ± 1.424 |

Data are expressed as mean ± S.D.

C. K⁺ Effects at pH 7

There was a tendency for the solubility of calcium to increase with an increase in potassium concentration, however, the difference is not significant, p>0.05 (Table 30). No calcium could be detected in preparations using Caltrate™.

Similar observations to that of calcium were obtained for the solubility of magnesium and zinc (p>0.05) in all formulas containing acetate salts (Tables 31-32). No measurable magnesium and zinc was reported for preparations using Caltrate™.

TABLE 30

Effect Of Concentration Of K⁺ On The Solubility Of Calcium Of Each Formula At pH 7

| K+ Conc. (mM) | The solubility of calcium (g/L) | | | | | |
|---|---|---|---|---|---|---|
| | Caltrate ™ | Ca ACE | A1 | A4 | A5 | A6 |
| 0 | 0.133 ± 0.051 | 98.950 ± 19.224 | 101.353 ± 12.947 | 37.637 ± 2.509 | 48.670 ± 2.102 | 23.337 ± 3.162 |
| 10 | — | 144.000 ± 14.731 | 66.800 ± 1.539 | 32.100 ± 0.361 | 64.033 ± 8.892 | 17.100 ± 0.173 |
| 50 | — | 174.467 ± 79.146 | 68.533 ± 3.259 | 33.933 ± 2.515 | 64.867 ± 17.244 | 19.033 ± 3.630 |
| 100 | — | 156.333 ± 64.361 | 68.600 ± 5.356 | 30.500 ± 3.672 | 82.000 ± 35.508 | 20.667 ± 2.363 |
| 140 | — | 130.033 ± 32.461 | 60.400 ± 25.999 | 56.767 ± 32.771 | 68.400 ± 7.100 | 42.000 ± 18.340 |
| 170 | — | 134.567 ± 55.048 | 126.133 ± 72.997 | 68.433 ± 29.905 | 64.800 ± 26.352 | 30.900 ± 14.912 |

Data are expressed as mean ± S.D.
No statistical differences in all K⁺ concentrations tested for all formulations tested.

TABLE 31

Effect Of Concentration Of K⁺ On The Solubility Of Magnesium Of Each Formula At pH 7

| K+ Conc. (mM) | The solubility of magnesium (g/L) | | | | | |
|---|---|---|---|---|---|---|
| | Caltrate ™ | CaACE | A1 | A4 | A5 | A6 |
| 0 | 0.093 ± 0.006 | 0.527 ± 0.121 | 0.173 ± 0.015 | 34.697 ± 4.836 | 23.927 ± 1.747 | 41.797 ± 5.622 |
| 10 | — | 0.767 ± 0.189 | 0.140 ± 0.010 | 32.033 ± 2.829 | 30.967 ± 2.136 | 46.800 ± 3.158 |
| 50 | — | 1.027 ± 0.587 | 0.347 ± 0.316 | 33.533 ± 2.084 | 31.867 ± 8.151 | 48.200 ± 1.253 |
| 100 | — | 0.807 ± 0.278 | 0.183 ± 0.047 | 34.067 ± 3.465 | 39.233 ± 16.350 | 54.000 ± 2.955 |
| 140 | — | 0.817 ± 0.303 | 0.160 ± 0.035 | 57.833 ± 34.279 | 32.833 ± 5.541 | 90.467 ± 42.518 |
| 170 | — | 0.760 ± 0.310 | 0.230 ± 0.062 | 64.200 ± 26.513 | 31.333 ± 12.507 | 61.900 ± 30.685 |

Data are expressed as mean ± S.D.
No statistical differences in all K⁺ concentrations tested for all formulations tested.

TABLE 32

A Effect Of Concentration Of K⁺ On The Solubility Of Zinc Of Each Formula At pH 7

| K⁺ Conc. (mM) | The solubility of zinc (g/L) | | | | | |
|---|---|---|---|---|---|---|
| | Caltrate™ | CaACE | A1 | A4 | A5 | A6 |
| 0 | 0.007 ± 0.012 | 0.030 ± 0.010 | 1.283 ± 0.220 | 1.980 ± 0.256 | 2.637 ± 0.143 | 1.440 ± 0.140 |
| 10 | — | 0.293 ± 0.110 | 0.727 ± 0.064 | 1.173 ± 0.163 | 3.243 ± 0.725 | 1.090 ± 0.070 |
| 50 | — | 0.627 ± 0.437 | 1.140 ± 0.036 | 1.447 ± 0.135 | 3.127 ± 0.720 | 1.247 ± 0.045 |
| 100 | — | 0.257 ± 0.110 | 1.197 ± 0.068 | 1.587 ± 0.106 | 3.417 ± 1.252 | 1.460 ± 0.122 |
| 140 | — | 0.387 ± 0.186 | 0.827 ± 0.506 | 2.583 ± 0.755 | 2.747 ± 1.432 | 2.607 ± 1.301 |
| 170 | — | 0.287 ± 0.142 | 1.223 ± 0.541 | 2.437 ± 0.618 | 2.873 ± 0.771 | 1.720 ± 0.624 |

Data are expressed as mean ± S.D.

TABLE 33

Concentration Of Ions In Human Gastric And Intestinal Fluids

| | Concentration of ion (mM) | |
|---|---|---|
| Ions | In Stomach/Gastric Fluid[a] | In Intestine/Intestinal Fluid[a] |
| Na⁺ | 0-100 (0-80) | (155) |
| K⁺ | 0-10 (0-15) | (70-150) |
| H⁺ | 1-140 (20-120) | (pH 7.7-8.2) |
| Cl⁻ | 100-170 (120-160) | (30-90) |
| Phosphate ions | | Up to 100** |
| HCO₃⁻ | | (70-130) |

[a]Values were cited from The Digestive System (ISBN 0443062455). The values in brackets were cited from The Medical Physiology (ISBN 0781719364).
**based on the solubility of sodium phosphate.

EXAMPLE 6

In Vivo Evaluation of Calcium, Magnesium and Zinc Balance

The objectives of the balance studies were to evaluate the effects of dietary conditions and formulations on calcium, magnesium and zinc balance.

A. Dietary Conditions

Two diets, one with normal calcium and the other is calcium free, were used for the studies. The nutrient composition of the diets are listed on Table 34:

TABLE 34

Composition Of Normal And Calcium Free Diet

| | Normal | Calcium Free |
|---|---|---|
| Protein, % | 24.0 | 19.0 |
| Fat, % | 4.5 (ether extract) 6.0 (acid hydrolysis) | 10.0 |
| Cholesterol, ppm | 101 | 48 |
| Fiber, % | 5.3 | 5.4 |
| Carbohydrates, % | 21.5 (starch) 0.2 (Glucose) 0.2 (Fructose) 3.4 (Sucrose) 0.6 (Lactose) | 60.6 |
| Potassium, % | 1.20 | 0.62 |
| Sodium, % | 0.40 | 0.27 |
| Chlorine, % | 0.70 | 0.27 |
| Calcium, % | 0.95 | 0.0 |
| Magnesium, % | 0.25 | 0.07 |
| Zinc, % | 0.011 | 0.0031 |
| Iron, ppm | 290 | 60 |
| Manganese, ppm | 110 | 65 |
| Copper, ppm | 17 | 23.9 |
| Vitamin K, ppm | 3.2 | 10.4 |
| Riboflavin, ppm | 12 | 20.0 |
| Pyridoxine, ppm | 8.0 | 16.5 |

B. Materials and Methods

Male Sprague-Dawley rats (about 6-7 weeks), with an initial weight between 220 g to 250 g, were randomly divided into different treatment groups. All the rats were housed in individual metabolic cages in a temperature-controlled room. Each rat received free access to the normal diet (Table 34) before the experiment. Both normal and calcium free diets (Table 34) were used in this set of studies. De-ionized water was provided ad libitum. All the rats were weighed before treatment.

C. Treatments

There were two set of studies performed: a normal diet and calcium free diet. In each study, there were seven treatment groups. Thirty five animals were randomly assigned to one of the treatment groups: Caltrate™, Calcium Acetate (CaACE), A1, A4, A5, A4 plus vitamin $D_3$ and A5 plus vitamin $D_3$ (n=5 per group). Rats participating in the normal diet study received normal diet ad libitum throughout. Rats participating in the group of calcium free diet received the calcium free food ad libitum starting five days before and throughout treatment. In both study groups, animals received one dose a day for five days. Contents of calcium, magnesium and zinc in individual formulation and in each diet were determined using ICP-OES. Values of dosage and dietary intake were measured for the calculation of elemental balance. For rats that were fed the normal diet, average daily elemental intake of calcium, magnesium and zinc was 625, 155 and 10 mg/kg/day, respectively. Daily elemental dosages, similar to that of human's, are 53.14 mg/kg for calcium, 0.38 to 55 mg/kg/day for magnesium and 0.017 to 2.5 mg/kg/day for zinc. Vitamin $D_3$, 1.06 μg/kg/day (42.512 IU/kg/day; 1 IU=0.025 μg), was added to each dosage preparation prior to administration. The vehicle for preparing each dose was de-ionized water. The concentration of calcium in all dosage preparations was 15.94 mg/mL. One mL of each preparation was administered by gavage. Body weight, elemental dosage and diet consumption were recorded daily.

D. Sample Collection, Handling and Analysis

Animals were housed individually in a metabolic cage five days before the study. Food consumption was evaluated daily.

Urine and feces were collected daily for four days and the content of calcium, magnesium and zinc was determined. On Day 5, each animal received its treatment. Each animal was anesthetized shortly before peak blood collection with a heparinized syringe via cardiac puncture. Immediately after blood collection, the animal was then sacrificed with an overdose of isoflourane. Each blood sample was centrifuged at 1900 rpm at room temperature; plasma was harvested and stored at −20° C. until analysis. Urine was measured daily; it was diluted with de-ionized water, filtered and an aliquot was stored at −20° C. until analysis. Daily fecal output was collected and lyophilized. Each sample was weighed and digested using a mixture of three volume of nitric acid and one volume of perchloric acid. For every gram of dried feces, 10 mL of acid mixture was added. Each sample was digested for three days. The volume of the digested sample was measured and an aliquot of the digest was stored at −20° C. until analysis. The content of calcium, magnesium and zinc in plasma, feces and urine were determined using ICP-OES.

In general, urinary excretion accounted for less than 5% of fecal excretion. Therefore, fecal excretion practically determines the quantity of elemental balance.

E. Statistical Analysis

All results were analyzed using two-way ANOVA. $P<0.05$ was considered to be significantly different. The data are presented as mean±S.D. and mean±S.E.M. in tables and figures, respectively.

F. Results: Calcium Free Diet

Table 35 shows the body weight of rats during the study. Stools from study animals were soft and this observation could be related to low elemental intake. Insufficient elements from the diet and dosage may have also caused the lack of weight gain for this set of animals. When compared to the Caltrate™ group, the body weight of the animals in groups A4 and A5 plus vitamin $D_3$ was significantly higher, suggesting higher elemental intake (Table 35).

TABLE 35

Body Weight Of Rats In Each Treatment Group With Calcium Free Diet (n = 5)

| Treatment group | Body weight of rats (g) | | | | |
|---|---|---|---|---|---|
| | Day 1 | Day 2 | Day 3 | Day 4 | Day 5 |
| Caltrate ™ | 184.6 ± 7.7 | 178.6 ± 9.9 | 177.2 ± 8.8 | 179.2 ± 13.7 | 175.4 ± 14.2 |
| Ca ACE | 202.4 ± 9.3 | 194.8 ± 9.3$^\$$ | 196.8 ± 10.9 | 193.4 ± 11.9$^\$$ | 188.0 ± 12.2$^\$$ |
| A1 | 190.4 ± 11.9 | 185.6 ± 14.0* | 187.6 ± 10.9 | 186.6 ± 11.3$^\$$ | 182.8 ± 15.4* |
| A4 | 188.4 ± 12.9$^{\$*+}$ | 184.2 ± 13.2$^{\$*+}$ | 184.0 ± 12.7 | 182.4 ± 13.5$^{\$*+}$ | 183.2 ± 14.0* |
| A5 | 187.8 ± 8.8$^{\&\#}$ | 184.0 ± 6.0$^{\$\&\#}$ | 184.2 ± 5.6$^{\$*\#}$ | 185.4 ± 6.0$^{\$*+\&\#}$ | 182.4 ± 9.2$^{*\#}$ |
| A4 + Vit D | 207.6 ± 11.9$^{\$*+\&}$ | 200.0 ± 5.2$^{\$+}$ | 198.6 ± 4.5$^{\$*+\&}$ | 204.2 ± 4.4$^{\$\&@}$ | 199.8 ± 6.4$^{\$+\&}$ |
| A5 + Vit D | 204.8 ± 14.4$^{\$*+\&\%}$ | 195.6 ± 8.3$^{\$+\%}$ | 196.4 ± 7.7$^{+\&\%}$ | 201.0 ± 5.0$^{\$\&\%}$ | 196.8 ± 8.2$^{\$+}$ |

$^\$$P < 0.05, compared with Caltrate ™;
*P < 0.05, compared with Ca ACE;
$^+$P < 0.01, compared with A1;
$^\&$P < 0.05, compared with A4;
$^\%$P < 0.001, compared with A5;
$^\#$P < 0.001, compared with A4 + Vit D;
$^@$P < 0.05, compared with A5 + Vit D.

Daily calcium balance was calculated using equation 1:

$$Ca\ Balance = total\ Ca\ intake(dose\ and\ dietary\ intake) - Ca\ excreted\ in\ urine - Ca\ excreted\ in\ feces \quad (1)$$

While, percentage of Ca balance was determined using equation 2:

$$\%\ Ca\ balance = Ca\ balance/(total\ Ca\ intake) \times 100\% \quad (2)$$

Cumulated calcium balance and % cumulated net calcium balance were calculated using equations (1) and (2), except, the sum of daily intake and excretion was used for calculation. The balance for magnesium and zinc was also calculated using the concept of equations (1) and (2). Cumulated elemental balance and % cumulated net elemental balance were calculated in a similar fashion as described above.

The addition of magnesium and zinc to a formula promotes the retention of calcium. A1, a composition with miniscule amounts of magnesium and zinc, has a lower calcium retention (17%, Table 36); whereas the retention of calcium is significantly higher when the ratio of Ca/Mg was increased to 2/1 (A5), the calcium retention is 49% (Table 36). A higher proportion of magnesium, such as that present in A4, does not produce more changes in calcium retention (49%, Table 36). From the calcium retention standpoint, it appears a 2/1 Ca/Mg ratio is optimal.

Figure 2:
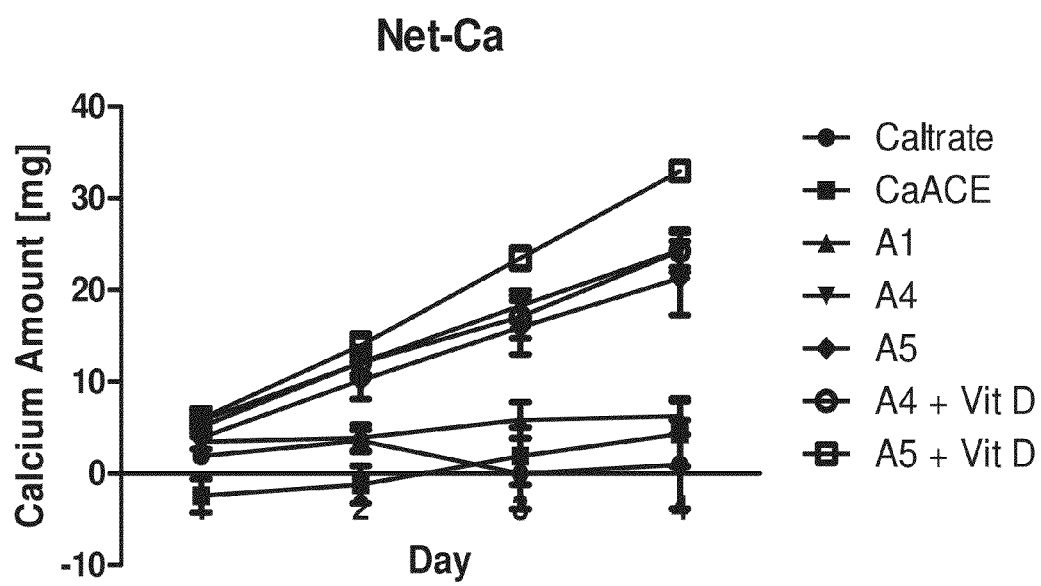
FIG. 2 shows the average cumulative net amount of calcium retained (±S.E.M.) in rats receiving a calcium free diet over a four day period.

The addition of vitamin $D_3$ increases calcium retention significantly (FIG. 2 and Table 36). Calcium retention increased to 62% when vitamin $D_3$ was added to A5 (Table 36). This value is more than five times higher than that of the Caltrate™ and CaACE groups.

TABLE 36

Cumulative Net Percentage Of Calcium In Rats Treated With Elemental Supplements While Receiving Calcium Free Diet (n = 5 per group)

| Treatment group | Cumulative net percentage of calcium (%) | | | |
|---|---|---|---|---|
| | Day 1 | Day 2 | Day 3 | Day 4 |
| Caltrate ™ | 23.8 ± 15.9* | 22.3 ± 16.8 | −2.27 ± 40.0 | 0.734 ± 35.7 |
| Ca ACE | −30.6 ± 51.3 | −9.88 ± 26.5 | 4.88 ± 24.0 | 11.1 ± 20.0 |

TABLE 36-continued

Cumulative Net Percentage Of Calcium In Rats Treated With Elemental Supplements While Receiving Calcium Free Diet (n = 5 per group)

| Treatment group | Cumulative net percentage of calcium (%) | | | |
|---|---|---|---|---|
| | Day 1 | Day 2 | Day 3 | Day 4 |
| A1 | 37.5 ± 18.7* | 20.9 ± 15.5 | 20.8 ± 15.0 | 17.2 ± 12.1 |
| A4 | 40.9 ± 19.1* | 48.6 ± 13.7* | 49.1 ± 10.2$* | 49.1 ± 7.7$* |
| A5 | 36.4 ± 24.1* | 46.8 ± 19.5* | 48.7 ± 18.4$* | 48.6 ± 19.1$* |
| A4 + Vit D | 46.6 ± 22.3* | 50.3 ± 10.9* | 47.9 ± 14.8$* | 50.8 ± 11.2$* |
| A5 + Vit D | 43.7 ± 19.2* | 52.7 ± 11.8* | 59.2 ± 7.6$*+ | 62.0 ± 5.2$*+ |

$P < 0.05, compared with Caltrate ™;
*: P < 0.05, compared with Ca ACE;
+P < 0.05, compared with A1;
: P < 0.05, compared with A4 + Vit D.

Figure 3:
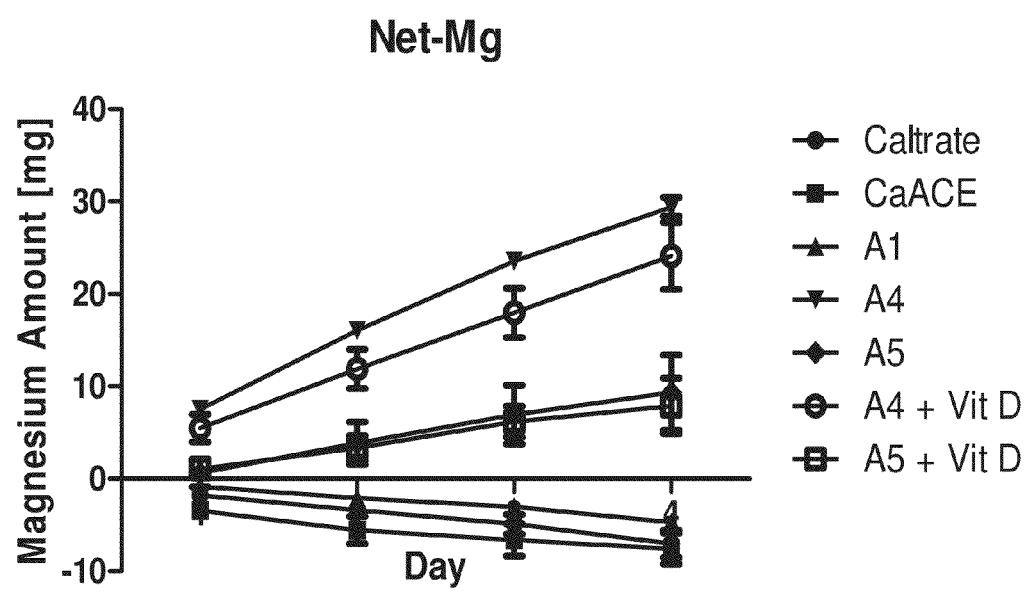
FIG. 3 shows the cumulative net amount of magnesium retained (±S.E.M.) in rats receiving calcium free diet over a four day period.

Magnesium appears to be required in order to maintain magnesium balance (Table 37). Formulas (Caltrate™, CaACE and A1) that have miniscule amounts of magnesium caused a net loss of magnesium (FIG. 3 and Table 37).

The addition of vitamin $D_3$ has no significant effect on the retention of magnesium. The cumulative net percentage of magnesium did not change significantly after vitamin $D_3$ was added to A4 and A5 (FIG. 3 and Table 37).

Figure 4:
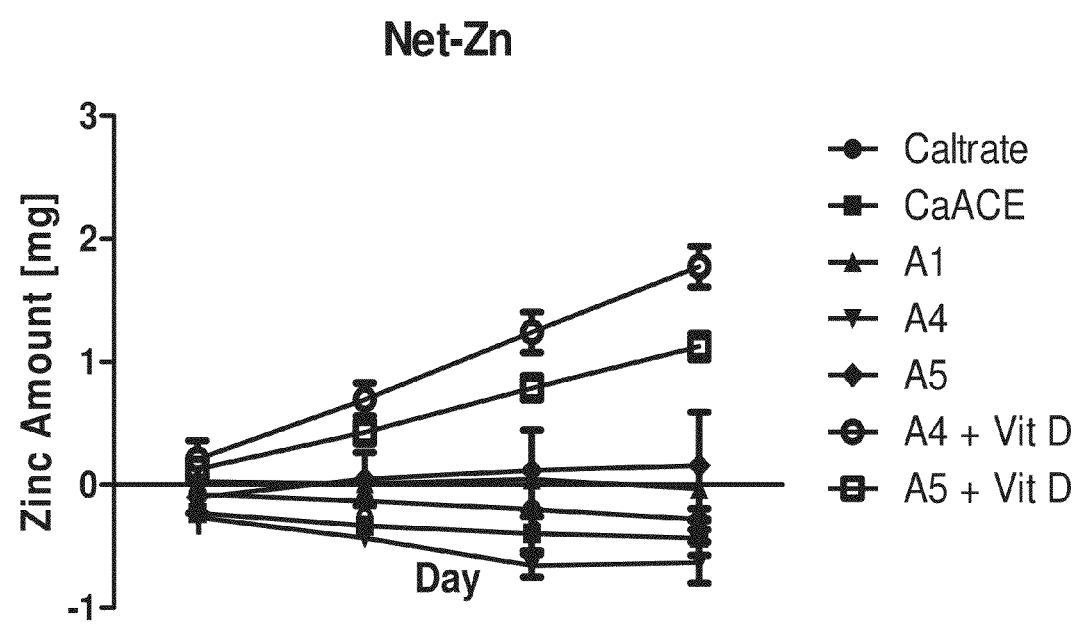
FIG. 4 shows the cumulative net amount of zinc retained (±S.E.M.) in rats receiving calcium free diet over a four day period.

However, the addition of vitamin $D_3$ to A4 and A5 made zinc balance positive (FIG. 4 and Table 38). The importance of vitamin $D_3$ on zinc is clearly demonstrated in this set of studies.

FIG. 5 shows plasma elemental profiles after each treatment. There were no significant differences observed after elemental treatments.

TABLE 37

Cumulative Net Percentage Of Magnesium In Rats Treated With Elemental Supplements While Receiving Calcium Free Diet (n = 5 per group)

| Treatment group | Cumulative net percentage of magnesium (%) | | | |
|---|---|---|---|---|
| | Day 1 | Day 2 | Day 3 | Day 4 |
| Caltrate ™ | −191.9 ± 139.1 | −125.6 ± 51.0 | −111.8 ± 39.1 | −116.5 ± 37.7 |
| Ca ACE | −197.2 ± 105.2 | −150.4 ± 88.9 | −115.3 ± 62.7 | −93.6 ± 37.2 |
| A1 | −47.3 ± 22.4$* | −67.9 ± 33.3* | −55.2 ± 13.4 | −64.4 ± 24.6 |
| A4 | 66.5 ± 8.7$*+ | 68.1 ± 6.4$*+ | 65.8 ± 5.9$*+ | 60.9 ± 4.7$*+ |
| A5 | 23.7 ± 46.3$* | 37.6 ± 37.1$*+ | 41.1 ± 34.2$*+ | 39.6 ± 33.3$*+ |
| A4 + Vit D | 46.3 ± 27.5$*+ | 49.3 ± 18.8$*+ | 49.3 ± 15.3$*++ | 48.9 ± 15.5$*+ |
| A5 + Vit D | 16.0 ± 20.0$* | 23.9 ± 21.5$*+ | 28.9 ± 17.9$*+ | 27.2 ± 23.0$*+ |

$P < 0.05, compared with Caltrate ™;
*: P < 0.05, compared with Ca ACE;
+P < 0.05, compared with A1.

The retention of zinc is highly variable; it is particularly true with formulas such as Caltrate™, calcium acetate and A1 that contain minute amounts of zinc (Table 38). The results also show that zinc balance became negative when the amount of zinc is low.

The addition of zinc to formulas such as A4 and A5 did not significantly improve zinc balance (Table 38). The addition of magnesium to the formulas may have caused zinc balance to stay negative (FIG. 4).

TABLE 38

Cumulative Net Percentage Of Zinc In Rats Treated With Elemental Supplements While Receiving Calcium Free Diet (n = 5 per group)

| Treatment group | Cumulative net percentage of zinc | | | |
|---|---|---|---|---|
| | Day 1 | Day 2 | Day 3 | Day 4 |
| Caltrate ™ | −50.6 ± 50.0 | −38.7 ± 23.8 | −36.9 ± 26.4 | −39.5 ± 23.7 |
| Ca ACE | −107.1 ± 85.5 | −77.7 ± 59.0 | −65.7 ± 66.7 | −50.5 ± 46.4 |
| A1 | 10.1 ± 8.7& | −0.348 ± 22.2& | 4.22 ± 7.3& | −2.79 ± 6.4 |
| A4 | −61.0 ± 38.8& | −55.3 ± 29.3& | −58.3 ± 24.5$ | −33.8 ± 23.9$ |

TABLE 38-continued

Cumulative Net Percentage Of Zinc In Rats Treated With
Elemental Supplements While Receiving Calcium Free Diet (n = 5
per group)

| Treatment group | Cumulative net percentage of zinc | | | |
|---|---|---|---|---|
| | Day 1 | Day 2 | Day 3 | Day 4 |
| A5 | −8.05 ± 45.3$&  | 9.737 ± 39.5$*& | 9.96 ± 40.3$*& | 8.76 ± 40.1$* |
| A4 + Vit D | 27.2 ± 40.7$*& | 43.7 ± 18.8$*& | 51.2 ± 15.1$*& | 54.2 ± 11.2*& |
| A5 + Vit D | 22.8 ± 17.9*& | 35.8 ± 17.8*& | 42.9 ± 12.9*& | 44.6 ± 10.1*& |

$P < 0.05, compared with Caltrate ™;
*: P < 0.05, compared with Ca ACE;
&P < 0.05, compared with A4

G. Results: Normal Diet

Rats that received normal diet gained weight (Table 39). Elemental treatments have no significant effect on weight gain (p>0.05).

TABLE 39

Body Weight Of Rats Receiving Normal Calcium Diet (n = 5)

| Treatment group | Body weight of rats (g) | | | | |
|---|---|---|---|---|---|
| | Day 1 | Day 2 | Day 3 | Day 4 | Day 5 |
| Caltrate ™ | 228.8 ± 4.6 | 232.8 ± 2.6 | 233.8 ± 3.5 | 243.6 ± 8.9 | 243.8 ± 5.1 |
| Ca ACE | 242.0 ± 7.4 | 237.0 ± 12.5 | 239.2 ± 13.9 | 238.6 ± 13.9 | 244.0 ± 12.8 |
| A1 | 230.0 ± 4.5 | 233.8 ± 8.0 | 238.2 ± 6.1 | 244.6 ± 7.2 | 244.6 ± 3.5 |
| A4 | 234.8 ± 7.7 | 238.6 ± 5.1 | 238.2 ± 5.9 | 239.0 ± 5.1 | 245.8 ± 4.9 |
| A5 | 239.6 ± 10.3 | 243.0 ± 13.9 | 245.4 ± 13.6 | 245.4 ± 13.4 | 248.6 ± 14.4 |

Data are expressed as mean ± S.D.

Figure 6:
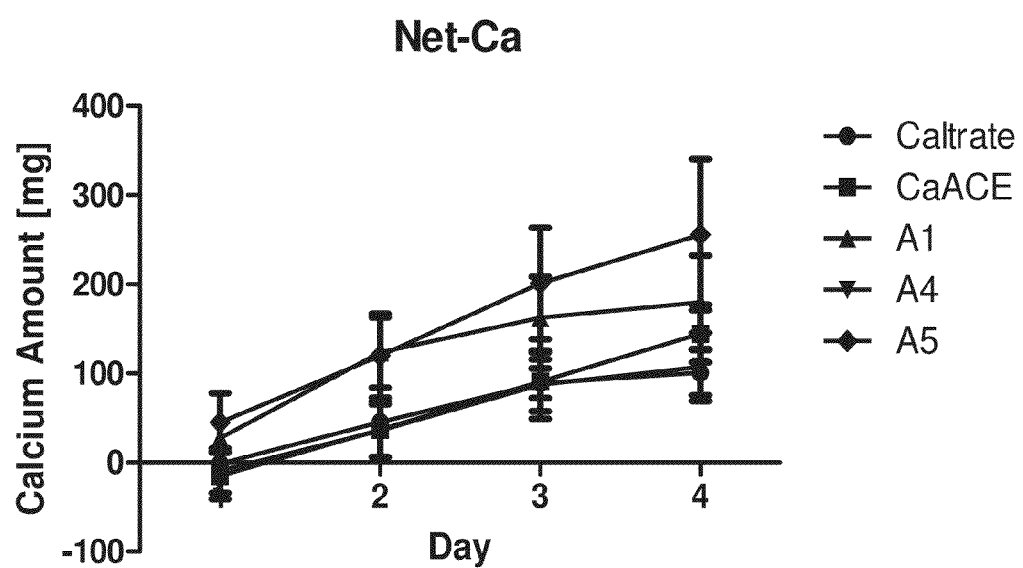
FIG. 6 shows the average cumulative net amount of calcium retained (±S.E.M.) in rats receiving normal diet over a four day period.

The pattern of calcium retention appears to be similar to that obtained from rats that received calcium free diet (compare Tables 36 and 40); suggesting calcium balance is dependent upon elemental treatments, despite the fact that the amount of calcium administered was approximately 10% of the animal's daily dietary intake (~130 to 140 mg of calcium per day). This observation strongly suggests that dietary calcium, present in the least absorbable carbonate form, was enhanced by elemental treatments. The treatment with Caltrate™ has minimal effect. It is not surprising because Caltrate™ contains only calcium carbonate. The treatment with A5 has the most pronounced effect (FIG. 6 and Table 40).

TABLE 40

Cumulative Net Percentage Of Calcium In Rats Treated With
Elemental Supplements While Receiving Normal Diet (n = 5 per group)

| Treatment group | Cumulative net percentage of calcium (%) | | | |
|---|---|---|---|---|
| | Day 1 | Day 2 | Day 3 | Day 4 |
| Caltrate ™ | −6.9 ± 24.6 | 17.3 ± 7.5 | 21.3 ± 10.0 | 17.5 ± 10.2 |
| Ca ACE | 14.4 ± 24.0 | 26.9 ± 9.0 | 30.3 ± 4.9 | 31.9 ± 3.0 |
| A1 | 31.4 ± 33.5$ | 49.2 ± 38.8$ | 39.2 ± 27.3 | 31.3 ± 21.9 |
| A4 | 19.3 ± 12.6 | 23.7 ± 9.4 | 26.2 ± 9.6 | 22.7 ± 7.3 |
| A5 | 52.1 ± 21.7$*& | 49.0 ± 19.8$ | 48.9 ± 20.4 | 45.3 ± 22.7 |

$P < 0.05, compared with Caltrate ™;
*: P < 0.05, compared with Ca ACE;
&P < 0.05, compared with A4

Figure 7:
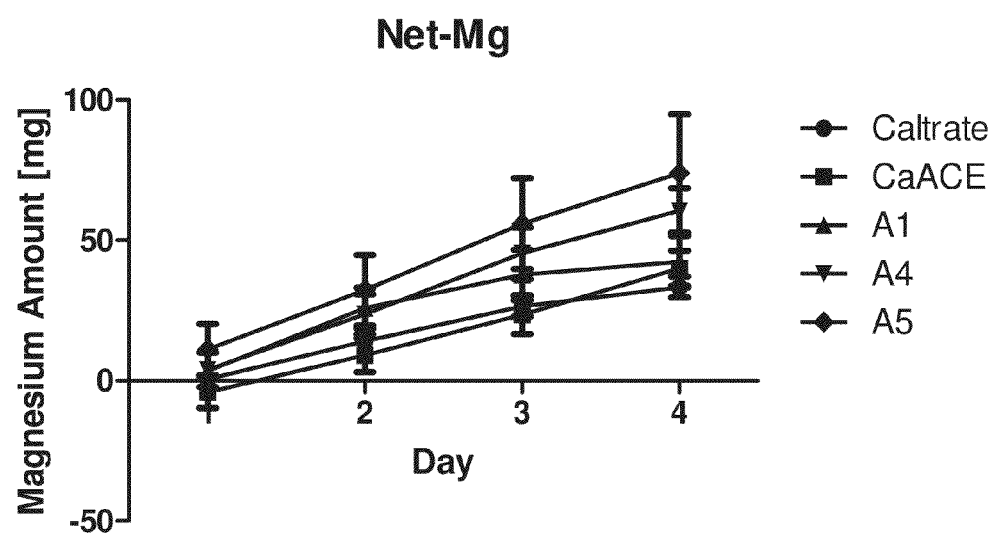
FIG. 7 shows the average cumulative net amount of magnesium retained (±S.E.M.) in rats receiving normal diet over a four day period.

Average dietary intake of magnesium by the study animals was approximately 35 mg. Magnesium balance for all study groups was positive (FIG. 7 and Table 41). This observation is consistent with the observation obtained from animals receiving calcium free diet, in that magnesium intake is required to maintain a positive balance (Tables 37 and 41). Interestingly, the day to day trend showed that animals treated with acetate formulas (CaACE, A1, A4 and A5 vs. Caltrate™) have consistently higher percentage of magnesium balance.

TABLE 41

Cumulative Net Percentage Of Magnesium In Rats Treated With
Elemental Supplements While Receiving Normal Diet (n = 5 per group)

| Treatment group | Net accumulative percentage of magnesium (%) | | | |
|---|---|---|---|---|
| | Day 1 | Day 2 | Day 3 | Day 4 |
| Caltrate ™ | −2.82 ± 19.6% | 23.3 ± 8.1% | 27.3 ± 10.0 | 24.6 ± 6.9 |
| Ca ACE | 16.7 ± 17.2% | 29.9 ± 3.8 | 34.3 ± 2.5 | 37.7 ± 2.7 |
| A1 | 11.7 ± 11.7% | 44.1 ± 30.7 | 38.9 ± 22.9 | 31.5 ± 17.0 |
| A4 | 28.2 ± 9.1$ | 34.0 ± 7.8 | 36.8 ± 7.2 | 35.0 ± 4.4 |
| A5 | 48.9 ± 25.3 | 48.9 ± 20.9 | 50.6 ± 20.1 | 48.6 ± 21.0 |

$P < 0.05, compared with Caltrate ™;
%P: <0.05, compared with A5

Figure 8:
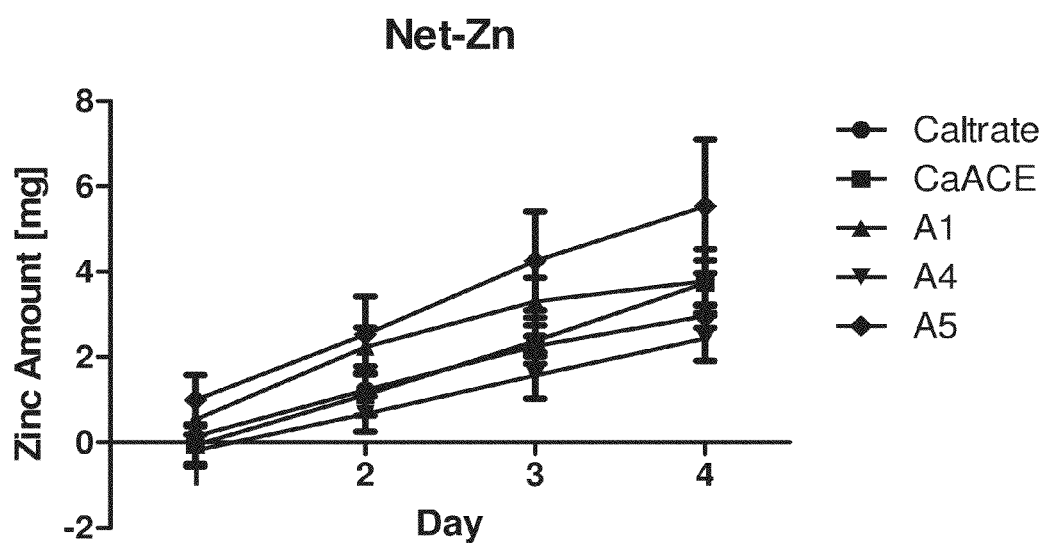
FIG. 8 shows the average cumulative net amount of zinc retained (±S.E.M.) in rats receiving normal diet over a four day period.

There were no statistical differences among elemental treatments in terms of zinc balance (FIG. 8 and Table 42). The quantity of zinc administered via elemental formulas was no more than 30% of the daily dietary intake. It was noted that the addition of a high quantity of magnesium tended to lower zinc balance, a trend observed with A4 treatment (FIG. 8 and Table 42). This observation is similar to that observed in the calcium free diet study (Table 38).

Contrary to the calcium free diet study (Table 38), zinc balance was positive in this study (Table 42). This was achieved without vitamin $D_3$ (FIGS. 4 and 8, Tables 38 and 42). This apparent discrepancy may be due to the quantity of total zinc intake and/or the rate at which zinc was consumed. Elemental consumption, along with other nutrients, occurred throughout the feeding period which may last up to 12 hours;

whereas elemental treatments were given as a bolus. Concentration and ratio of nutrients presented to the intestinal wall may have a huge difference between bolus administration and dietary consumption. These differences could account for the difference in zinc balance.

The results from the calcium free and normal diet studies clearly suggest that adequate dietary intake of elements is key to elemental balance. Elemental and vitamin $D_3$ supplementation are necessary if the diet in deficient in these nutrients.

Figure 9:
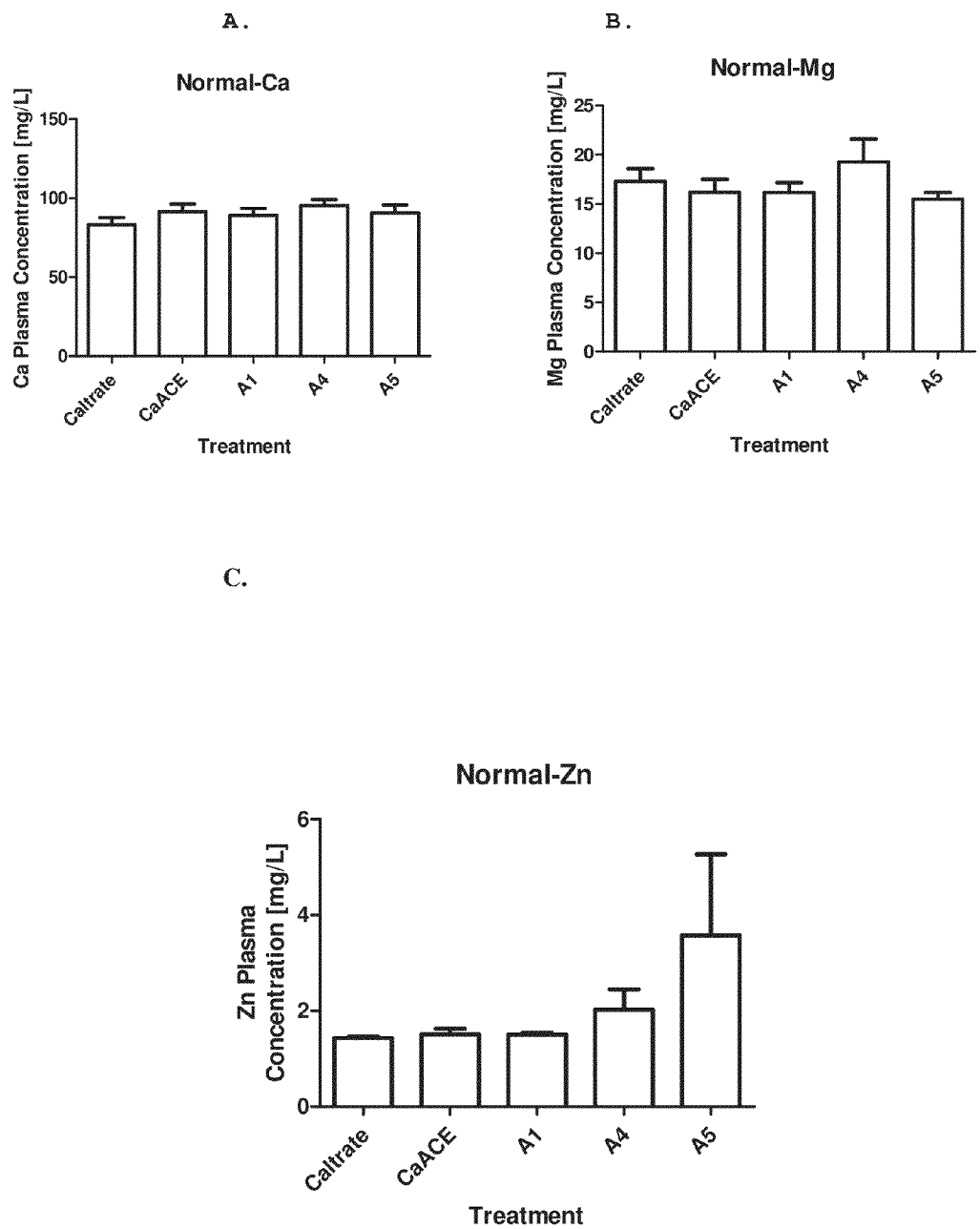
FIG. 9 shows the plasma calcium (A), magnesium (B) and zinc (C) levels sampled from rats at the end of the treatment period while receiving normal diet.

FIG. 9 shows plasma concentration of calcium, magnesium and zinc after individual elemental treatments. There were no statistical differences in the concentration of these elements in plasma after elemental treatments ($P>0.05$).

TABLE 42

Cumulative Net Percentage Of Zinc In Rats Treated With Elemental Supplements While Receiving Normal Diet (n = 5 per group)

| Treatment group | Cumulative net percentage of zinc (%) | | | |
| --- | --- | --- | --- | --- |
| | Day 1 | Day 2 | Day 3 | Day 4 |
| Caltrate ™ | 0.67 ± 34.7% | 29.5 ± 7.5 | 33.8 ± 10.2 | 32.0 ± 7.8 |
| Ca ACE | 27.5 ± 16.0% | 40.9 ± 7.3 | 45.6 ± 5.9 | 48.4 ± 4.4 |

TABLE 42-continued

Cumulative Net Percentage Of Zinc In Rats Treated With Elemental Supplements While Receiving Normal Diet (n = 5 per group)

| Treatment group | Cumulative net percentage of zinc (%) | | | |
| --- | --- | --- | --- | --- |
| | Day 1 | Day 2 | Day 3 | Day 4 |
| A1 | 26.6 ± 11.2% | 50.8 ± 26.8 | 46.3 ± 20.4 | 38.7 ± 18.8 |
| A4 | 17.7 ± 10.3% | 24.9 ± 6.3% | 27.6 ± 7.2 | 27.6 ± 5.0 |
| A5 | 54.7 ± 21.9 | 52.6 ± 21.7 | 53.8 ± 21.0 | 51.2 ± 23.0 |

%P < 0.05, compared with A5

H. Results: Calcium Free Diet with Daily Consumed Doses of Calcium

The objective of this study was to evaluate elemental balance when the daily intake of calcium, magnesium and zinc was replaced with elemental treatments. Animals, received de-ionized water ad libitum (DI Water group), were fed normal calcium diet. Animals, substituting their daily calcium intake by A1 or A5, were fed calcium free diet. It is apparent that the gavage procedure did not have an effect on the body weight of the animals (Table 43). Elemental treatments, however, induced a significant reduction in body weight.

TABLE 43

Body Weight Of Rats Receiving Calcium Free Diet And Daily Consumed Doses Of Calcium (n = 4)

| Treatment group | Body weight of rats (g) | | | | |
| --- | --- | --- | --- | --- | --- |
| | Day 1 | Day2 | Day3 | Day4 | Day5 |
| DI Water | 200.8 ± 2.50 | 207.0 ± 3.9 | 209.0 ± 8.7 | 209.5 ± 9.9 | 215.5 ± 11.7 |
| A1 | 198.0 ± 9.1 | 183.5 ± 7.7 | 178.3 ± 8.1 | 180.8 ± 10.2 | 186.0 ± 8.0 |
| A5 | 194.0 ± 8.2 | 182.3 ± 7.1 | 179.8 ± 7.2 | 179.0 ± 7.7 | 181.5 ± 6.8 |

Note:
There is no statistical significant difference between A1 and A5.
There is statistical difference between A1 and DI ($p < 0.001$), and between A5 and DI ($p < 0.001$).

Figure 10:
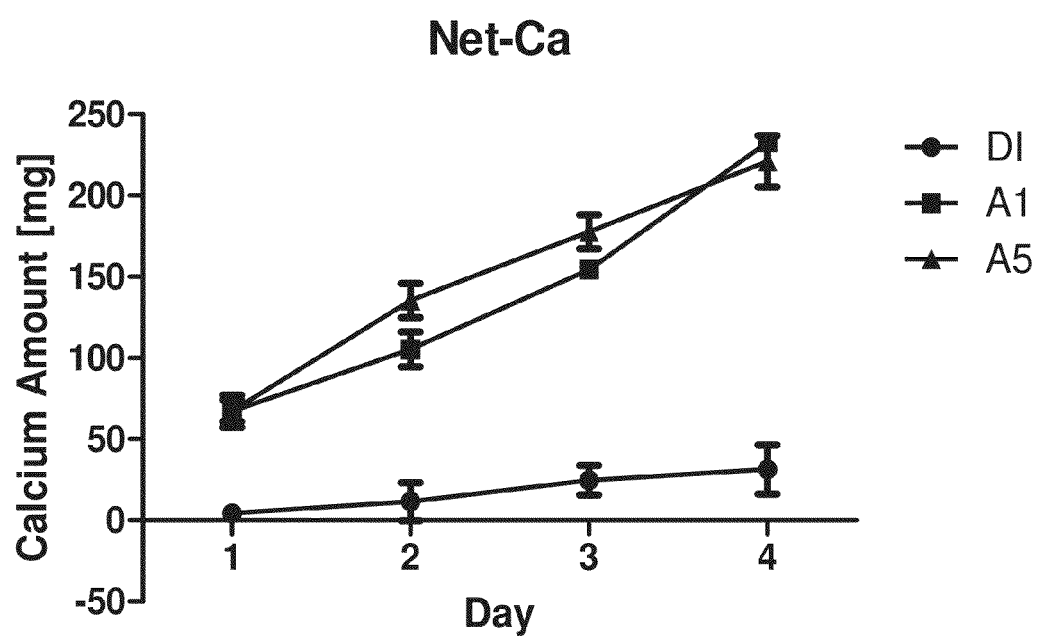
FIG. 10 shows the cumulative net amount of calcium retained (±S.E.M.) in rats receiving calcium free diet plus a daily consumed dose of calcium over a four day period.

Contrary to the results obtained from the normal and calcium free diet studies, magnesium has a minor effect in enhancing calcium retention (FIG. 10 and Table 44). The administration of a soluble form of calcium, calcium acetate, significantly enhanced calcium balance (FIG. 10 and Table 44).

TABLE 44

Cumulative Net Percentage Of Calcium In Rats Treated With A Daily Consumed Dose Of Calcium While Receiving Calcium Free Diet (n = 4 per group)

| Treatment group | Net accumulative percentage of Ca (%) | | | |
| --- | --- | --- | --- | --- |
| | Day 1 | Day 2 | Day 3 | Day 4 |
| DI Water | 2.87 ± 5.4 | 3.89 ± 7.6 | 5.72 ± 4.3 | 5.41 ± 5.2 |
| A1 | 46.3 ± 14.7* | 37.7 ± 8.9* | 37.4 ± 1.3* | 42.7 ± 3.1* |
| A5 | 54.9 ± 12.7* | 56.7 ± 10.3*@ | 50.4 ± 7.5* | 47.4 ± 8.0* |

*: $P < 0.05$, when compared with DI;
@$P < 0.05$ m when compared to A1

Figure 11:
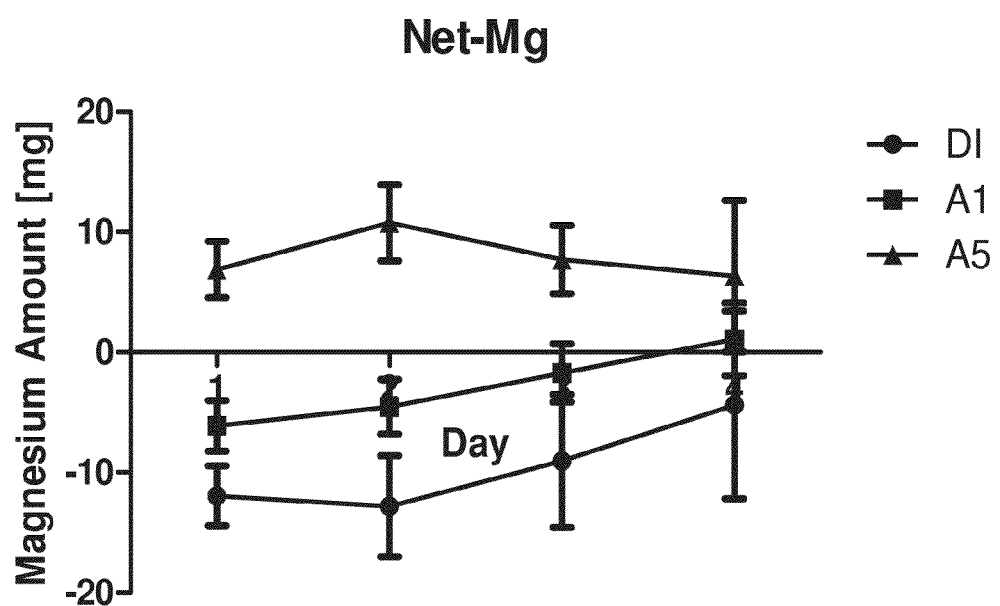
FIG. 11 shows the cumulative net amount of magnesium retained (±S.E.M.) in rats receiving calcium free diet plus a daily consumed dose of calcium over a four day period.

Consistent with the calcium free diet study described above, magnesium was required to maintain a positive magnesium balance (FIG. 11 and Table 45).

TABLE 45

Cumulative Net Percentage Of Magnesium In Rats Treated With A Daily Consumed Dose Of Calcium While Receiving Calcium Free Diet (n = 4 per group)

| Treatment group | Net accumulative percentage of Mg (%) | | | |
| --- | --- | --- | --- | --- |
| | Day 1 | Day 2 | Day 3 | Day 4 |
| DI Water | −32.2 ± 12.4 | −17.0 ± 10.4 | −7.9 ± 10.0 | −2.59 ± 10.4 |
| A1 | −75.9 ± 50.0* | −27.6 ± 27.7 | −6.54 ± 19.4 | 3.6 ± 18.0 |
| A5 | 18.3 ± 12.7*@ | 14.4 ± 8.6@ | 7.0 ± 5.2 | 4.4 ± 8.4 |

*: $P < 0.05$, when compared with DI;
@$p < 0.05$ m when compared to A1

Figure 12:
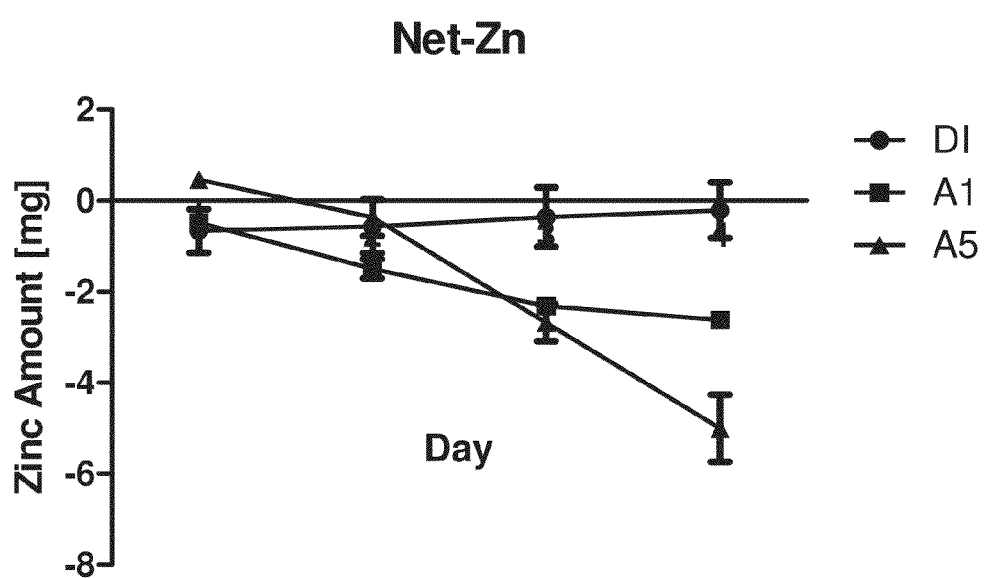
FIG. 12 shows the cumulative net amount of zinc retained (±S.E.M.) in rats receiving calcium free diet plus a daily consumed dose of calcium over a four day period.

Despite a higher amount of zinc administered with A5, zinc balance was significantly lower than that of the DI Water group, providing further support that high calcium and magnesium concentration in the intestine could have diminished zinc absorption. (FIG. 12 and Table 46). The amounts of zinc administered between the DI Water and A1 groups were similar. However, similar to that of A5, zinc balance was significantly lower than that of DI Water (FIG. 12 and Table 46); suggesting high solution concentration of calcium in the intestine may interfere with zinc absorption.

This set of results suggest that elemental dietary intake of elements does not produce the same effects when compared to that of an equivalent bolus dose.

Taking all the study results into consideration, A5 produces the most consistent calcium balance under different experimental/dietary conditions (compare results on Tables 36, 40 and 44). The addition of vitamin $D_3$ enhances calcium retention of A5 when the subject is deficient in dietary elements (Table 36).

Figure 13:
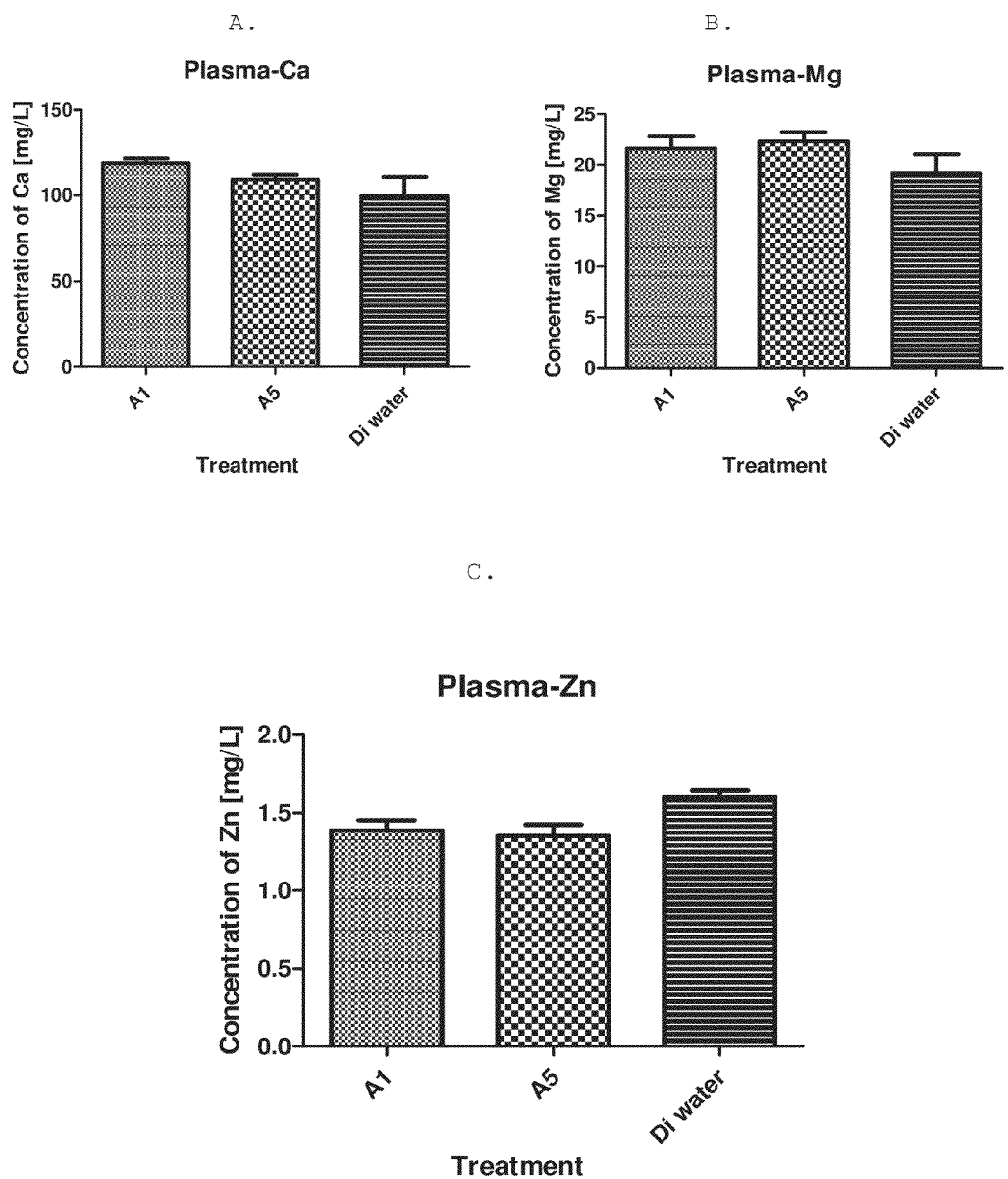
FIG. 13 shows the plasma calcium (A), magnesium (B) and zinc (C) levels sampled from rats at the end of the treatment period while receiving calcium free diet and a normal daily dose of calcium.

FIG. 13 shows plasma concentrations of calcium, magnesium and zinc after each elemental treatment. No statistical differences were found in these profiles ($P>0.05$).

TABLE 46

Cumulative Net Percentage Of Zinc In Rats Treated With A Daily Consumed Dose Of Calcium While Receiving Calcium Free Diet (n = 4 per group)

| Treatment group | Net accumulative percentage of Zn (%) | | | |
| --- | --- | --- | --- | --- |
| | Day 1 | Day 2 | Day 3 | Day 4 |
| DI Water | −26.5 ± 37.7 | −10.8 ± 22.9 | −4.45 ± 17.3 | −1.80 ± 12.2 |
| A1 | −42.9 ± 25.9 | −67.3 ± 16.3* | −69.5 ± 7.3* | −58.5 ± 6.2* |
| A5 | 23.7 ± 16.2*@ | −9.09 ± 19.3@ | −45.1 ± 11.8* | −63.2 ± 16.2* |

*: $P < 0.05$, when compared with DI;
@$p < 0.05$, when compared to A1

EXAMPLE 7

The objectives of this study were to evaluate the effects of salt, mineral composition and vitamins on the rate of bone loss in an ovariectomized rat model.

One hundred 4.5-month-old female Sprague-Dawley rats were used and housed at the Laboratory Animal Services Center at the Chinese University of Hong Kong with 12-h light-night cycle. Free cage movement was allowed with access to the normal calcium pellets and tap water. Daily consumption of calcium was approximately 140 mg, similar to that recorded in animals who participated in the balance studies. Ovariectomy (OVX), the removal of ovaries from the female rats, was performed on all rats at 6-month of age with the exception of the sham control.

Three weeks after OVX, all the rats recovered from the trauma of the surgery. The rats were randomly divided into different treatment groups or control groups and each group contained six rats. Four calcium formulas (A1, A4, A5 and A6) and Caltrate™ were investigated in the present study. The Caltrate™ group served as an elemental treatment control. All formulas were dissolved in distilled water, while Caltrate™ was in suspension in distilled water. The solution or suspension was given to the rats daily for 8 weeks by gavages. The dose of all formulas was calculated based on a calcium dose of 53.14 mg/kg/day. Dose of vitamin $D_3$ and vitamin $K_2$ was 12.75 IU/kg/day (equivalent to 800 IU/70 kg man/day) and 1.71 μg/kg/day (equivalent to 120 μg/70 kg man/day), respectively. All the treated rats were weighed daily and the mass data were recorded. The rats in two control groups (sham control and normal control) were given the equivalent volume of distilled water in parallel. For the groups with the treatment of bisphosphonate, alendronate (14 μg/kg/2-week) was injected subcutaneously on the back of the rats once every two weeks.

At the end of 8 weeks, the rats were anesthetized using isoflourane. Blood sample was then taken via heart puncture.

The rats were then euthanized under anesthesia by neck dislocation, and right hip, right femur and right tibia of each rat were collected for analysis. Plasma was collected from blood samples centrifuged at 1500 g for 15 min. Plasma concentrations of calcium, magnesium, and zinc were measured using ICP-OES.

Results show that plasma calcium levels were not statistically different from that of the sham control ($p>0.05$) and the values are all within normal levels (90-110 mg/L). All plasma concentrations of Mg were within the normal range (18-36 mg/L). No significant difference in magnesium plasma concentrations was observed except normal control (without surgery) has a mean value higher than that of A4+Vit D+Vit K ($p<0.05$). Similarly, plasma concentrations of Zn in all rats reached the rat normal concentration at about 1.26 mg/L. Zn plasma concentrations of rats in the normal control was significantly higher than that of sham control rats and also the rats treated with A5+vitamin D and A4+vitamine D+vitamin K (p<0.05).

Figure 14:
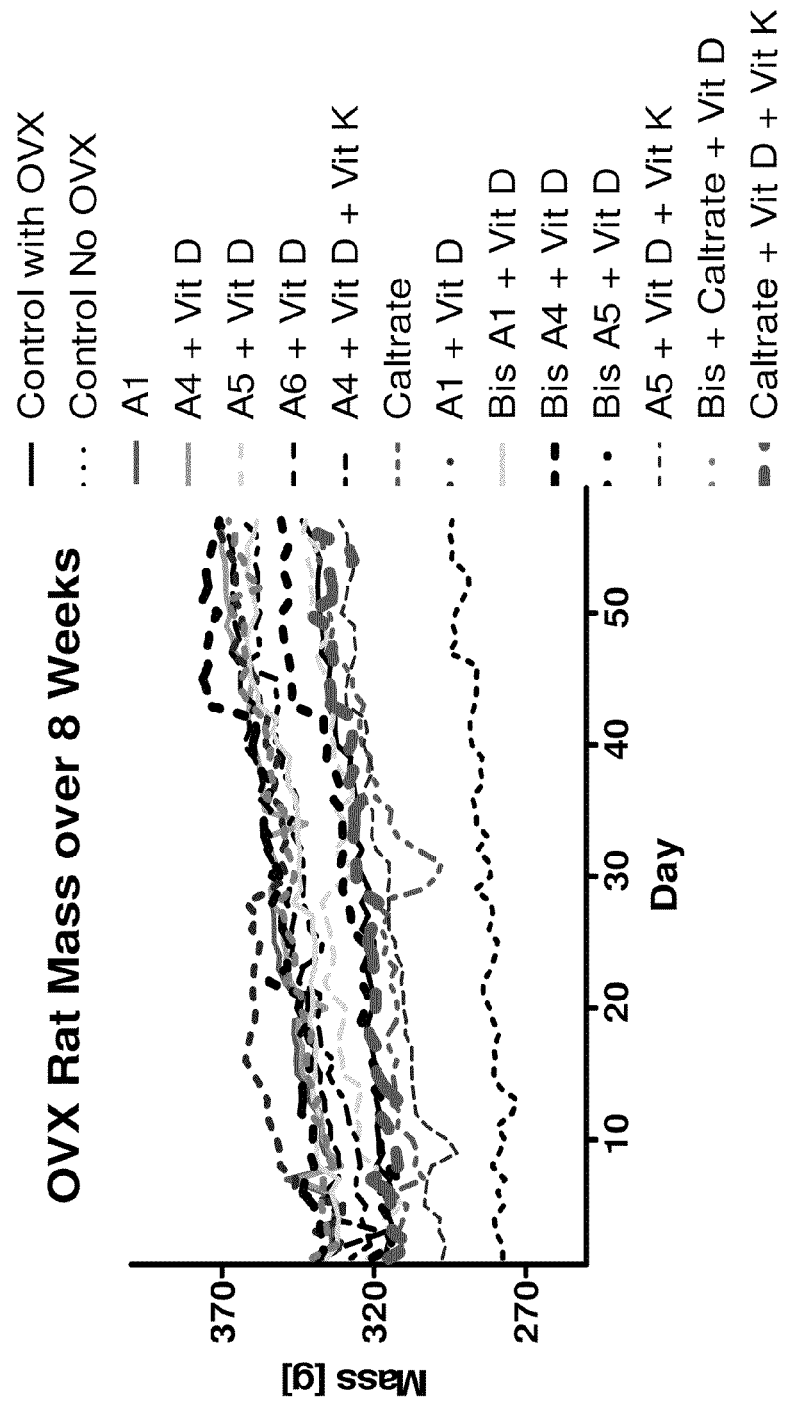
FIG. 14 is the body mass record of rats which received individual elemental treatments.

Body weight changes for different treatment groups are shown in FIG. 14. As expected, weight gains in the OVX rats were significantly greater than the normal rats (p<0.05).

Figure 15:
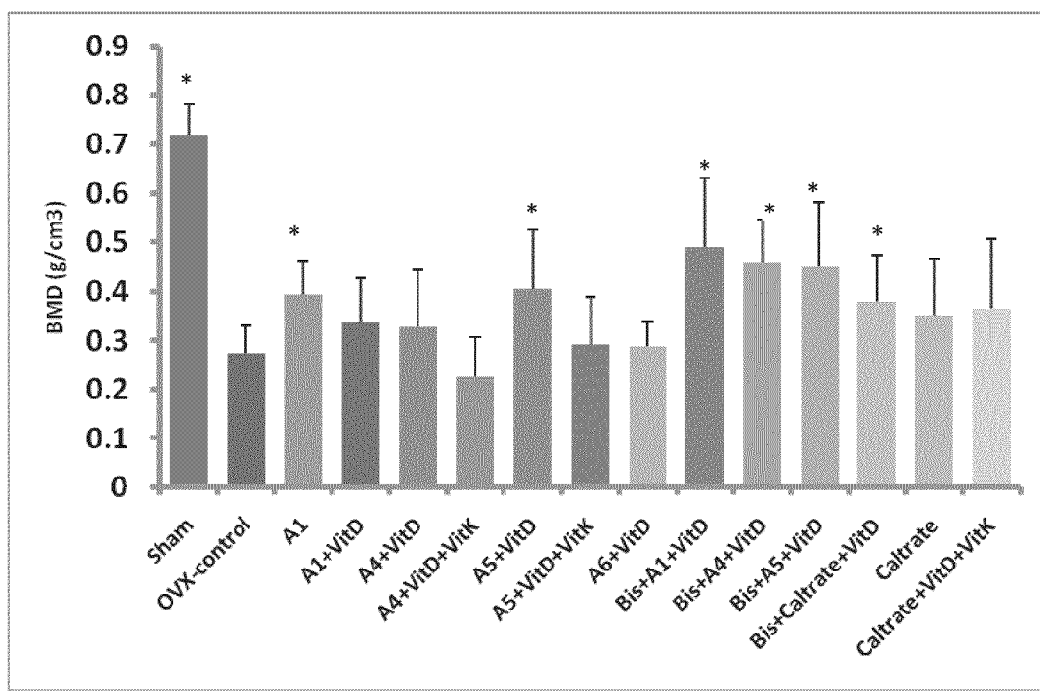
FIG. 15 shows trabecular BMD of Distal Femur Averaged from 3 pQCT Slices. *: significantly different from OVX-control ($p<0.05$).
Figure 16:
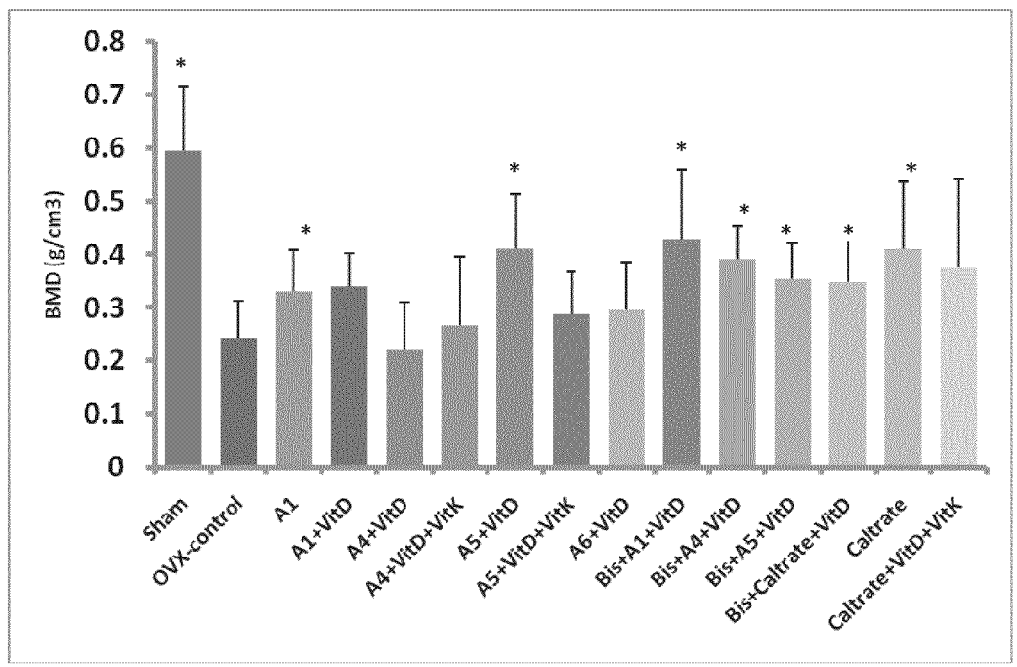
FIG. 16 shows trabecular BMD of Proximal Tibia Averaged from 3 pQCT Slices. *: significantly different from OVX-control ($p<0.05$).

The effects of test substances on bone mineral density (BMD) are shown on FIGS. 15 and 16. Trabecular BMD of Distal Femur BMD values of groups A1, A5+Vit D, Bis+A1+Vit D, Bis+A4+Vit D, Bis+A5+Vit D and Bis+Caltrate+Vit D are significantly higher than that of the OVX control (FIG. 15), suggesting these treatments significantly slow down the rate of loss of bone mass. The addition of vitamin K did not have any significant effect on reducing the rate of bone loss. Similar observations were obtained for the average values of trabecular BMD of Proximal Tibia, except the value of Caltrate™ was high enough to become statistically different (p<0.05, FIG. 16). Again, vitamin K did not have any significant contribution. The treatment with A5+Vit D provided consistently higher BMD at distal femur and proximal tibia, suggesting this formula may have an advantage over the other elemental formulas. Although, the addition of bisphosphonate provides consistently better results, the difference, when compared to A5+Vit D and other elemental formula, such as A1, was not significant (FIGS. 15 and 16).

The BMD results of A1 are similar to that of A5+vit D. This is not surprising because A1 animals were fed normal calcium diet which contains a significant amount of magnesium.

The OVX rat model used in this study did not permit evaluation of maximum bending force and failure energy after each treatment because the values obtained from the OVX control and that of the Sham were insignificantly different from each other (P>0.05).

EXAMPLE 8

Optimization of Elemental Formula

The objective of this example is to design an elemental formula which would provide an optimal mix of vitamin $D_3$ and acetate salts of calcium, magnesium and zinc.

In the study reported by Seelig et al. (2004), a high Ca/Mg ratio in a diet is associated with osteoporosis and unwanted cardiovascular events. The high dietary calcium intake in the last 50 years may be undesirable. Other investigators have shown that dietary calcium intake may not be a significant factor in determining bone density and therefore, osteoporosis in older men and women. Magnesium has been identified to be an important element in bone metabolism because it is essential for a number of enzymes which are involved in bone metabolism. Furthermore, when patients are diagnosed with osteoporosis, they invariably have low serum levels of magnesium. In addition, when dietary calcium is shown to improve bone density, magnesium is always present in a significant quantity.

The question is: What is the optimal ratio of calcium to magnesium? Are the ratios important? Seelig et al. (2004) found that a Ca/Mg ratio of 2/1, a dietary composition in the early 1900s, was associated with the least cardiovascular diseases. However, the optimal ratio of calcium to magnesium has not been carefully evaluated. An issue that needs to be addressed is the variability in solubility of calcium and magnesium salts. As shown in Table 3, difference in calcium solubility in artificial intestinal fluid could amount to over 25,000 fold. The relationship between solubility and bioavailability of calcium is generally considered to be unimportant, as it was demonstrated by several research groups (Tsugawa et al., 1995; Heaney et al., 2001). However, the number of calcium salts used was limited. In a study reported by Hanzlik et al. (2005), the solubility of calcium in the intestine plays a significant role in the bioavailability of calcium. Our animal results support the notion that calcium absorption is highly dependent on the salt form. Dependent on the diet condition, the difference in bioavailability between calcium carbonate and calcium acetate is at least 2-fold (Tables 36 and 40).

Interestingly, the story with magnesium is very similar (Coudray et al., 2005). The reported range of magnesium bioavailability ranged from 50 to 67%.

The only study that evaluated the effect of calcium and Ca/Mg ratio on bone density in postmenopausal women was performed by Abraham and Grewal (1990). The finding was that a ratio of Ca/Mg of 1/1.2 was significantly better than that of 1/0.4. The amount of calcium used in the study was 500 mg. The calcium salt used was calcium citrate and the magnesium salt used was magnesium oxide. According to the literature, the bioavailability of calcium citrate is 30% and it was not different from that of calcium carbonate (Heaney et al., 1999). The bioavailability of magnesium oxide is 50% (Coudray et al., 2005). If Ca/Mg ratio was to be calculated using bioavailable doses of calcium and magnesium, the Ca/Mg ratio employed by Abraham and Grewal (1990) would have been 1/2. The Abraham and Grewal study (1990) has established that magnesium is important in preventing osteoporosis. However, there was no definitive ratio set for Ca/Mg. This could be due to: a. the dosage of calcium; b. the availability of individual calcium salts; and c. the actual absorbable quantity of calcium and magnesium.

Our results show that there is a complex interplay between calcium, magnesium, zinc, vitamin $D_3$ and nutritional status on elemental balance (Examples 3 to 6).

Factors such as pH, cation and anion concentrations have different impacts on the solubility of calcium salts (Examples 3 to 5). The solubility of calcium in the form of calcium carbonate is extremely low under various experimental conditions, suggesting that the absorption of calcium will be low because the salt is not soluble along the entire GIT. The solubility of calcium in the form of calcium acetate is high and it is not affected significantly by pH, cations and anions. Cations tend to increase its solubility, but anions, such as bicarbonates, chloride and phosphate tend to reduce calcium solubility (Examples 3 to 5). Since the concentrations of cations and anions tested were within the physiological range (Table 33) and since there are opposing effects contributed by cations and anions, it is anticipated that that calcium acetate will remain in solution along GIT.

Magnesium is shown to enhance calcium absorption and balance (Example 6). Conversely, calcium and magnesium tend to diminish zinc balance. The intensity of the interplay is dependent on nutritional status of the animal. These complex interplays between the three elements can be nullified by the addition of vitamin $D_3$.

It has been suggested that dosage of calcium used for the past decades is too high and it should be trimmed to 750 mg. Since calcium carbonate is the most common form of calcium administered, it is equivalent to 180 mg of absorbable calcium, assuming a 24% bioavailability (Bo-Linn et al., 1984). The daily magnesium requirement is 310 mg and it is equivalent to 155 to 186 mg of bioavailable magnesium, assuming a 50 to 60% bioavailability of organic magnesium (Coudray et al., 2005).

In one embodiment, the bioavailability of calcium is at least three-fold higher when it is given as a blend of A5 and vitamin $D_3$ when compared to calcium carbonate (Example 6, Tables 36 and 40). Thus, the daily requirement of calcium from A5 and vitamin $D_3$ would be one third of that reported by (Bo-Linn et al., 1984) which is 250 mg of calcium.

In this invention, magnesium was found to enhance calcium balance (Example 6). Therefore, it is necessary to have magnesium in the formula. If 250 mg of calcium in the form of calcium acetate is administered, a Ca/Mg ratio of 2/1 and 1/1 would provide 125 mg and 250 mg of magnesium, respectively. This would translate to 62.5 to 125 mg of absorbable magnesium, respectively, assuming a 50% bioavailability.

A5 plus vitamin $D_3$ has the best average in reducing the rate of bone loss in an OVX model (FIGS. 15 and 16). These results are consistent with that obtained in the balance study (Example 6). Calcium carbonate, as represented by Caltrate™ did not show any significant improvement over OVX control when the Distal Femur BMD was used for comparison (FIG. 15).

Zinc has been shown to be essential for bone formation and the recommended daily allowance is 20 mg. It is found that zinc balance is dependent on nutritional status (Example 6). However, a positive zinc balance can be maintained if vitamin $D_3$ is incorporated into the formula.

Vitamin $D_3$ has been reported to increase the absorption of calcium from the gut; it also assists distribution of calcium into bone (Wasserman, 2004). We also found that vitamin $D_3$ is essential for calcium and zinc balance (Example 6). The recommended daily intake is 400 to 800 IU. This dosage is incorporated into the fortified extract.

It is also found that administration of A5 plus vitamin $D_3$ improved elemental balance of dietary calcium and magnesium (Example 6). This observation is significant because the less available form of calcium and magnesium was improved. The implication is that if a subject does not have enough elements in his diet, the supplementation of a low dose of the optimized formula plus that from the dietary source will provide adequate elemental daily requirements. Therefore, a lower dosage of A5 and vitamin $D_3$ can be used for maintaining bone health and possibly preventing osteoporosis.

Taking into account the solubility of the elements, its taste and convenience of administration, a two gram daily dose of A5 (~220 mg calcium) plus vitamin $D_3$ will provide adequate amounts of elements and vitamin $D_3$ for the maintenance of bone health and prevention of osteoporosis.

EXAMPLE 9

Fortification of Juices with A5

Fruit juices contain a number of acids such as malic acid, citric acid, etc. which may alter the solubility and hence the recovery of the three key elements in A5; hence, changing the absorbability of these elements when administered in juice format.

The objectives of this study were to evaluate the effects of temperature and storage on the recovery of calcium, magnesium and zinc in A5 after mixing with filtered and unfiltered orange, grape and carrot juice.

A 2.6 g or 500 mg amount of A5 was weighed accurately and mixed with 330 ml of water or either filtered or unfiltered grape, orange or carrot juice. The specimens were prepared at either 4 or 21° C. The elemental content was measured using ICP-OES.

Small quantities of calcium, magnesium and zinc were found in orange, grape and carrot juice (Tables 47, 50 and 53). Temperature and filtration had no effects on the recovery of calcium, magnesium and zinc of A5 when 2.6 g of A5 was used for the study (Tables 48, 51 and 54).

TABLE 47

Content of the three key elements in fresh orange juice

| | Content (mg/L) | | |
|---|---|---|---|
| Sample | Ca | Mg | Zn |
| Fresh orange juice | 87.7 ± 0.87 | 115 ± 0.9 | 0.47 ± 0.03 |

Data are expressed as Mean ± S.D. (n = 3)

TABLE 48

Elemental recovery of the 3 key elements of A5 (2.6 g) in orange juice at 4° C. and 21° C.

| | Solubility (g/L) | | | | | |
|---|---|---|---|---|---|---|
| | Ca | | Mg | | Zn | |
| Sample | 4° C. | 21° C. | 4° C. | 21° C. | 4° C. | 21° C. |
| Unfiltered | 0.968 ± 0.006 | 0.997 ± 0.002 | 0.528 ± 0.007 | 0.542 ± 0.012 | 0.047 ± 0.004 | 0.045 ± 0.000 |
| Filtered | 0.978 ± 0.008 | 0.994 ± 0.008 | 0.521 ± 0.007 | 0.527 ± 0.002 | 0.045 ± 0.001 | 0.045 ± 0.003 |

Data are expressed as mean ± S.D.
(n = 3)

TABLE 49

Elemental recovery from 500 mg of A5 in 330 ml orange juice stored at 4° C.

| | Solubility (g/L) | | | | | |
|---|---|---|---|---|---|---|
| | Ca | | Mg | | Zn | |
| | Filtered | Unfiltered | Filtered | Unfiltered | Filtered | Unfiltered |
| Fresh | 0.273 ± 0.005 | 0.274 ± 0.009 | 0.170 ± 0.001 | 0.167 ± 0.003 | 0.0105 ± 0.0012 | 0.0089 ± 0.0003 |
| One Week | 0.272 ± 0.005 | 0.172 ± 0.017*** | 0.171 ± 0.001 | 0.104 ± 0.010*** | 0.0104 ± 0.0015 | 0.0139 ± 0.0088 |

Data are expressed as Mean ± S.D.
(n = 3)
***P < 0.001 comparing with fresh group

TABLE 50

Content of the three key elements in fresh grapefruit juice

| | Content (mg/L) | | |
|---|---|---|---|
| Sample | Ca | Mg | Zn |
| Fresh grapefruit juice | 48.2 ± 0.79 | 104 ± 1.6 | 0.536 ± 0.008 |

Data are expressed as mean ± S.D. (n = 3)

TABLE 51

Comparison of elemental recovery of A5 (2.6 g) in grapefruit juice at 4° C. and 21° C.

| | Solubility (g/L) | | | | | |
|---|---|---|---|---|---|---|
| | Ca | | Mg | | Zn | |
| Sample | 4° C. | 21° C. | 4° C. | 21° C. | 4° C. | 21° C. |
| Unfiltered | 0.958 ± 0.010 | 0.968 ± 0.016 | 0.515 ± 0.005 | 0.518 ± 0.010 | 0.046 ± 0.001 | 0.046 ± 0.001 |
| Filtered | 0.981 ± 0.018 | 0.975 ± 0.004 | 0.516 ± 0.027 | 0.520 ± 0.005 | 0.045 ± 0.002 | 0.048 ± 0.002 |

Data are expressed as mean ± S.D. (n = 3)

TABLE 52

Elemental recovery from A5 (2.6 g) in distilled water at 4 and 21° C.

| | Solubility (g/L) | | |
|---|---|---|---|
| Temperature | Ca | Mg | Zn |
| 4° C. | 0.875 ± 0.018 | 0.407 ± 0.000 | 0.024 ± 0.002 |
| 21° C. | 0.897 ± 0.016 | 0.404 ± 0.009 | 0.028 ± 0.001 |

Data are expressed as Mean ± S.D. (n = 3)

TABLE 53

Content of the three elements in fresh carrot juice

| | Content (mg/L) | | |
|---|---|---|---|
| Sample | Ca | Mg | Zn |
| Fresh carrot juice | 37.499 ± 4.613 | 75.279 ± 6.183 | 0.7045 ± 0.0195 |

Data are expressed as Mean ± S.D. (n = 3)

TABLE 54

Elemental recovery from A5 in 330 ml carrot juice stored at 4° C.

| | Solubility (g/L) | | | | | |
|---|---|---|---|---|---|---|
| | Ca | | Mg | | Zn | |
| | 2.6 grams | 500 mg | 2.6 grams | 500 mg | 2.6 grams | 500 mg |
| Fresh | 0.907 ± 0.018 | 0.196 ± 0.009 | 0.482 ± 0.013 | 0.151 ± 0.001 | 0.0235 ± 0.0022 | 0.0031 ± 0.0001 |
| One Week | 0.935 ± 0.033 | 0.188 ± 0.006 | 0.481 ± 0.016 | 0.150 ± 0.008 | 0.0491 ± 0.0094** | 0.0031 ± 0.0000 |

Data are expressed as Mean ± S.D. (n = 3)
***P < 0.01 comparing with fresh group Similarly, temperature has no effect on the recovery of A5 elements in distilled water (Table 52).

Storage at 4° C. for a week did not change the recovery of calcium, magnesium and zinc when 2.6 g of A5 was dissolved in 330 ml of filtered and unfiltered orange and grape juice (Tables 48 and 51). However, when 500 mg of A5 was used instead, the recovery of calcium and magnesium was significantly lowered from the unfiltered orange juice (Table 49). The lower recovery of calcium from unfiltered orange juice suggests that the pulp in orange juice may bind Ca and Mg in A5. Carrot juice did not have this problem (Table 54).

This set of studies suggests that A5 can be used to fortify a number of juices and water. The 2.6 g of A5 provides a daily requirement of the three key elements for the prevention of osteoporosis: 300 mg of calcium, 150 mg of magnesium and 5.6 mg of zinc. 500 mg of A5 is intended to provide a serving of these elements in the functional food format.

REFERENCES

Abraham G E and Grewal H (1990) A total dietary program emphasizing magnesium instead of calcium. Effect on the mineral density of calcaneous bone in postmenopausal women on hormonal therapy. *J Reprod Med* 35:503-507.

Abrams S A and Atkinson S A (2003) Calcium, magnesium, phosphorus and vitamin D fortification of complementary foods. *J Nutr* 133:2994S-2999S.

Abrams S A, Griffin I J and Herman S (2002) Using stable isotopes to assess the bioavailability of minerals in food fortification programs. *Food Nutr Bull* 23:158-165.

Angus R M, Pocock N A and Eisman J A (1988a) Nutritional intake of pre- and postmenopausal Australian women with special reference to calcium. *Eur J Clin Nutr* 42:617-625.

Angus R M, Sambrook P N, Pocock N A and Eisman J A (1988b) Dietary intake and bone mineral density. *Bone Miner* 4:265-277.

Bass M, Ford M A, Brown B, Mauromoustakos A and Keathley R S (2006) Variables for the prediction of femoral bone mineral status in American women. *South Med J* 99:115-122.

Basso L E, Ubbink J B, Delport R, Spies J and Vermaak W J (2000) Effect of magnesium supplementation on the fractional intestinal absorption of 45CaCl2 in women with a low erythrocyte magnesium concentration. *Metabolism* 49:1092-1096.

Bo-Linn G W, Davis G R, Buddrus D J, Morawski S G, Santa Ana C and Fordtran J S (1984) An evaluation of the importance of gastric acid secretion in the absorption of dietary calcium. *J Clin Invest* 73:640-647.

Cai J, Zhang Q, Wastney M E and Weaver C M (2004) Calcium bioavailability and kinetics of calcium ascorbate and calcium acetate in rats. *Exp Biol Med (Maywood)* 229:40-45.

Celotti F and Bignamini A (1999) Dietary calcium and mineral/vitamin supplementation: a controversial problem. *J Int Med Res* 27:1-14.

Coudray C, Rambeau M, Feillet-Coudray C, Gueux E, Tressol J C, Mazur A and Rayssiguier Y (2005) Study of magnesium bioavailability from ten organic and inorganic Mg salts in Mg-depleted rats using a stable isotope approach. *Magnes Res* 18:215-223.

Ellenbogen L and Buono L C (1999) Calcium dietary supplement, in (Office USPaT ed), American Cyanamid Company (Madison, N.J.), United States of America.

Hanzlik R P, Fowler S C and Fisher D H (2005) Relative bioavailability of calcium from calcium formate, calcium citrate, and calcium carbonate. *J Pharmacol Exp Ther* 313: 1217-1222.

Heaney R P (1993a) Nutritional factors in osteoporosis. *Annu Rev Nutr* 13:287-316.

Heaney R P (1993b) Thinking straight about calcium. *N Engl J Med* 328:503-505.

Heaney R P, Dowell M S and Barger-Lux M J (1999) Absorption of calcium as the carbonate and citrate salts, with some observations on method. *Osteoporos Int* 9:19-23.

Heaney R P, Dowell M S, Bierman J, Hale C A and Bendich A (2001) Absorbability and cost effectiveness in calcium supplementation. *J Am Coll Nutr* 20:239-246.

Hendricks L (2004) Calcium dietary supplement, in (Office USPaT ed), Rhodia Inc. (Cranbury, N.J.), United States of America.

Hunt C D and Johnson L K (2007) Calcium requirements: new estimations for men and women by cross-sectional statistical analyses of calcium balance data from metabolic studies. *Am J Clin Nutr* 86:1054-1063.

Ilich J Z, Brownbill R A and Tamborini L (2003) Bone and nutrition in elderly women: protein, energy, and calcium as main determinants of bone mineral density. *Eur J Clin Nutr* 57:554-565.

Ilich J Z and Kerstetter J E (2000) Nutrition in bone health revisited: a story beyond calcium. *J Am Coll Nutr* 19:715-737.

Jackson S D and Blumberg J B (1997) Dietary supplements, in (Office USPaT ed), Energetics, Inc. (New York, N.Y.), United States of America.

Kanders B, Dempster D W and Lindsay R (1988) Interaction of calcium nutrition and physical activity on bone mass in young women. *J Bone Miner Res* 3:145-149.

Krumhar K C and Johnson H A (2006) Composition for promoting healthy bone structure, in (Office USPaT ed), Metagenics, Inc. (San Clemente, Calif.), United States of America.

Lee H H, Prasad A S, Brewer G J and Owyang C (1989) Zinc absorption in human small intestine. *Am J Physiol* 256: G87-91.

Li J and Li X (1995) Producing method for mineralizing agent of active mineral food, in *State Intellectual Property Office of The P.R.C.* (P.R.C. SIPOoT ed), Peoples Republic of China.

Lowe N M, Lowe N M, Fraser W D and Jackson M J (2002) Is there a potential therapeutic value of copper and zinc for osteoporosis? *Proc Nutr Soc* 61:181-185.

Mazer T B, DeWille N T, Chandler M A, Ragan R J, Snowden G A, Geraghty M E, Johnson C D and Drayer L R (1997) Calcium supplement, in (Office USPaT ed), Abbott Laboratories (Abbott Park, Ill.), United States of America.

Meignant C and Stenger E (2004) Therapeutic combination of vitamin and calcium in unitary galenic tablet form, a method of obtaining it, and the use thereof, in (Office USPaT ed), Laboratorie Innothera, Societe Anonyme (Arcueil, FR), United States of America.

Mutlu M, Argun M, Kilic E, Saraymen R and Yazar S (2007) Magnesium, zinc and copper status in osteoporotic, osteopenic and normal post-menopausal women. *J Int Med Res* 35:692-695.

Record I R, Record S J, Dreosti I E and Rohan T E (1985) Dietary zinc intake of pre-menopausal women. *Hum Nutr Appl Nutr* 39:363-369.

Riis B, Thomsen K and Christiansen C (1987) Does calcium supplementation prevent postmenopausal bone loss? A double-blind, controlled clinical study. *N Engl J Med* 316: 173-177.

Saltman P D and Strause L G (1993) The role of trace minerals in osteoporosis. *J Am Coll Nutr* 12:384-389.

Seelig M S, Altura B M and Altura B T (2004) Benefits and risks of sex hormone replacement in postmenopausal women. *J Am Coll Nutr* 23:482 S-496S.

Smith J C, Jr., Morris E R and Ellis R (1983) Zinc: requirements, bioavailabilities and recommended dietary allowances. *Prog Clin Biol Res* 129:147-169.

Sultenfuss S (1996) Daily vitamin and mineral supplement for women, in (Office USPaT ed), United States of America.

Tsugawa N, Okano T, Higashino R, Kimura T, Oshio Y, Teraoka Y, Igarashi C, Ezawa I and Kobayashi T (1995) Bioavailability of calcium from calcium carbonate, DL-calcium lactate, L-calcium lactate and powdered oyster shell calcium in vitamin D-deficient or -replete rats. *Biol Pharm Bull* 18:677-682.

Tsugawa N, Yamabe T, Takeuchi A, Kamao M, Nakagawa K, Nishijima K and Okano T (1999) Intestinal absorption of calcium from calcium ascorbate in rats. *J Bone Miner Metab* 17:30-36.

Walsdorf N B, Alexandrides G and Pak C Y C (1991) Calcium supplementation by dicalcium citrate-lactate, in (Office USPaT ed), Board of Regents, The University of Texas System (Austin, Tex.) Mission Pharmacal Company (San Antonio, Tex.), United States of America.

Wasserman R H (2004) Vitamin D and the dual processes of intestinal calcium absorption. *J Nutr* 134:3137-3139.

What is claimed is:

1. A composition consisting of about 4%-23% by weight of calcium in the form of calcium acetate, about 5.6%-9% by weight of magnesium in the form of magnesium acetate, about 0.2%-1.0% percent by weight of zinc in the form of zinc acetate, and 400 to 1200 IU of vitamin $D_3$ per 220mg of calcium, wherein said composition comprises more bioavailable calcium per unit weight than calcium carbonate or calcium citrate, a weight ratio of calcium to magnesium of 0.5:1 to 2:1, and a weight ratio of zinc to calcium of 0.05:1 to 0.2:1.

2. The composition of claim 1, wherein the composition comprises a daily dose of 5-40 mg of zinc.

3. The composition of claim 1, wherein the composition comprises a daily dose of 400 to 3000 IU of vitamin $D_3$.

4. The composition of claim 1, wherein the composition comprises a daily dose of 50 to 500mg of calcium and 25 to 500 mg of magnesium.

5. The composition of claim 1, wherein the composition comprises a daily dose of 100 to 300mg of calcium and 50 to 150mg of magnesium.

6. A juice composition comprising the composition of claim 1.

7. A method for alleviating or treating symptoms of osteoporosis in humans or animals, comprising the step of administering the composition of claim 1 to said humans or animals.

8. A method for increasing bone mineral density in humans or animals, comprising the step of administering the composition of claim 1 to said humans or animals.

* * * * *